(12) United States Patent
Rogers et al.

(10) Patent No.: US 11,832,948 B2
(45) Date of Patent: *Dec. 5, 2023

(54) INTRAOPERATIVE MONITORING OF NEUROMUSCULAR FUNCTION WITH SOFT, TISSUE-MOUNTED WIRELESS DEVICES

(71) Applicants: NORTHWESTERN UNIVERSITY, Evanston, IL (US); THE BOARD OF TRUSTEES OF THE UNIVERSITY OF ILLINOIS, Urbana, IL (US)

(72) Inventors: John A. Rogers, Wilmette, IL (US); Michel Kliot, Evanston, IL (US); Roozbeh Ghaffari, Cambridge, MA (US); YuHao Liu, Urbana, IL (US)

(73) Assignees: NORTHWESTERN UNIVERSITY, Evanston, IL (US); THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 98 days.

This patent is subject to a terminal disclaimer.

(21) Appl. No.: 17/557,392

(22) Filed: Dec. 21, 2021

(65) Prior Publication Data

US 2022/0110564 A1 Apr. 14, 2022

Related U.S. Application Data

(63) Continuation of application No. 16/969,649, filed as application No. PCT/US2019/019166 on Feb. 22, 2019, now Pat. No. 11,246,522.

(Continued)

(51) Int. Cl.
*A61B 5/24* (2021.01)
*A61B 5/296* (2021.01)
(Continued)

(52) U.S. Cl.
CPC .............. *A61B 5/24* (2021.01); *A61B 5/0004* (2013.01); *A61B 5/25* (2021.01); *A61B 5/296* (2021.01);
(Continued)

(58) Field of Classification Search
CPC .............. A61B 5/24; A61B 2562/0219; A61B 5/02055; A61B 5/398; A61B 5/4821;
(Continued)

(56) References Cited

U.S. PATENT DOCUMENTS

| 11,246,522 B2 * | 2/2022 | Rogers .................. A61B 5/398 |
| 2013/0072775 A1 * | 3/2013 | Rogers ................. A61B 5/7246 607/45 |

* cited by examiner

Primary Examiner — Jon Eric C Morales
(74) Attorney, Agent, or Firm — Locke Lord LLP; Tim Tingkang Xia, Esq.

(57) ABSTRACT

The provided systems, methods and devices describe lightweight, wireless tissue monitoring devices that are capable of establishing conformal contact due to the flexibility or bendability of the device. The described systems and devices are useful, for example, for skin-mounted intraoperative monitoring of nerve-muscle activity. The present systems and methods are versatile and may be used for a variety of tissues (e.g. skin, organs, muscles, nerves, etc.) to measure a variety of different parameters (e.g. electric signals, electric potentials, electromyography, movement, vibration, acoustic signals, response to various stimuli, etc.).

72 Claims, 23 Drawing Sheets

Related U.S. Application Data

(60) Provisional application No. 62/634,440, filed on Feb. 23, 2018.

(51) Int. Cl.
*A61B 5/398* (2021.01)
*A61B 5/25* (2021.01)
*A61B 5/00* (2006.01)
*A61N 1/04* (2006.01)

(52) U.S. Cl.
CPC .............. *A61B 5/398* (2021.01); *A61B 5/742* (2013.01); *A61N 1/0456* (2013.01); *A61B 2562/164* (2013.01)

(58) Field of Classification Search
CPC ........ A61B 2505/05; A61B 2562/0209; A61B 2562/164; A61B 3/112; A61B 5/0004; A61B 5/002; A61B 5/02; A61B 5/021; A61B 5/02405; A61B 5/02416; A61B 5/0261; A61B 5/0295; A61B 5/0533; A61B 5/0836; A61B 5/1109; A61B 5/25; A61B 5/296; A61B 5/318; A61B 5/369; A61B 5/388; A61B 5/392; A61B 5/395; A61B 5/4824; A61B 5/4836; A61B 5/7203; A61B 5/7217; A61B 5/726; A61B 5/7264; A61B 5/7267; A61B 5/7275; A61B 5/7282; A61B 5/742; A61N 1/0456; B81B 2201/0214; B81B 2203/04; B81B 3/007
See application file for complete search history.

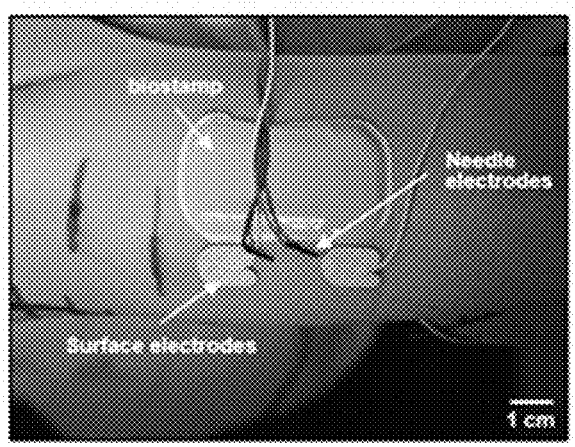
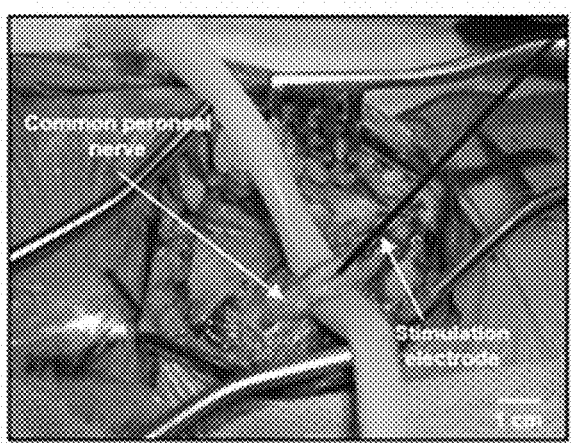
FIG. 2A
FIG. 2B
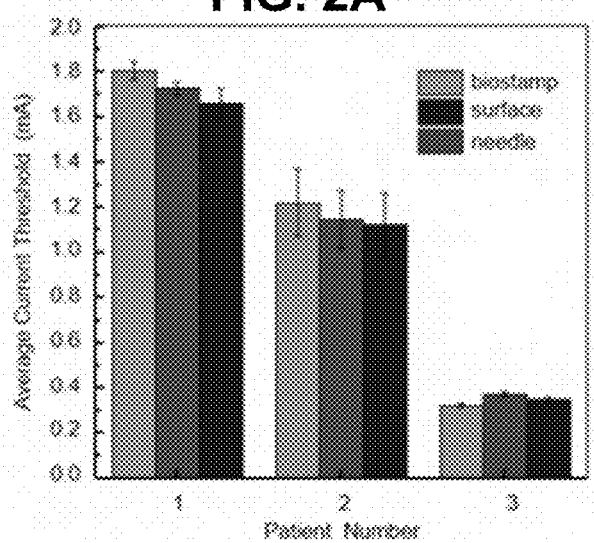
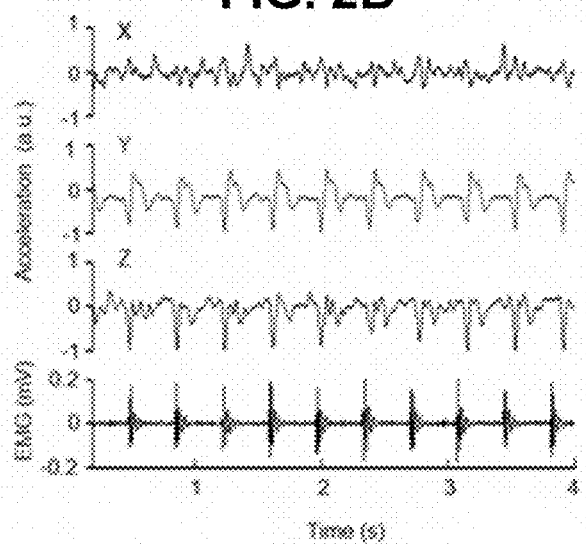
FIG. 2C
FIG. 2D

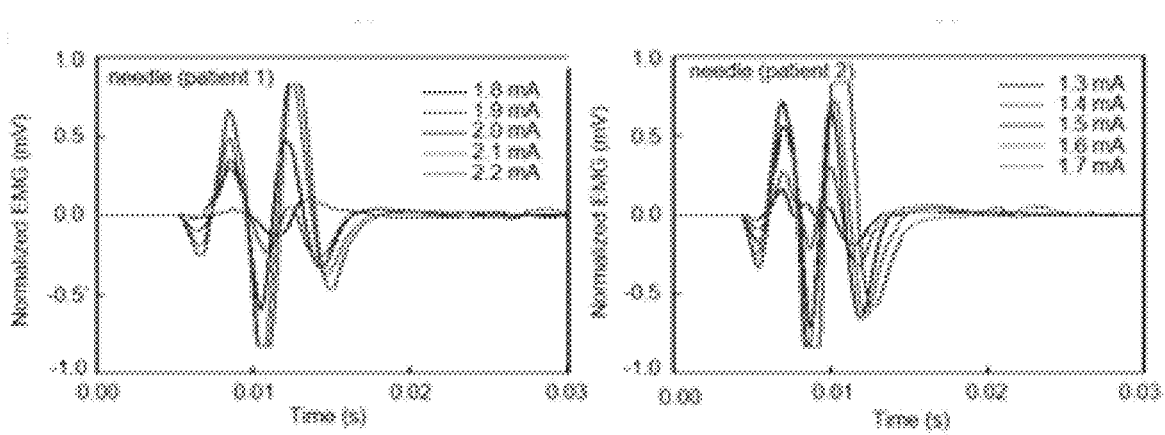
FIG. 3D  FIG. 3G
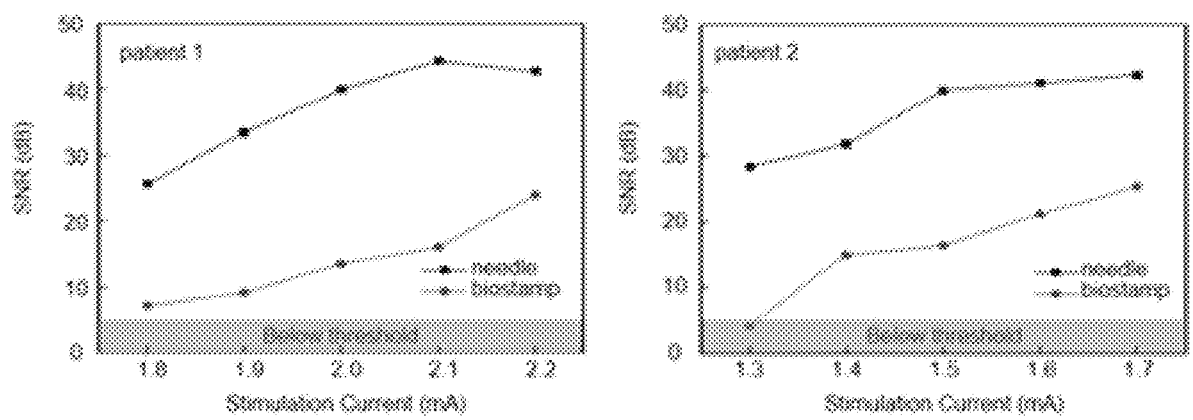
FIG. 3E  FIG. 3H

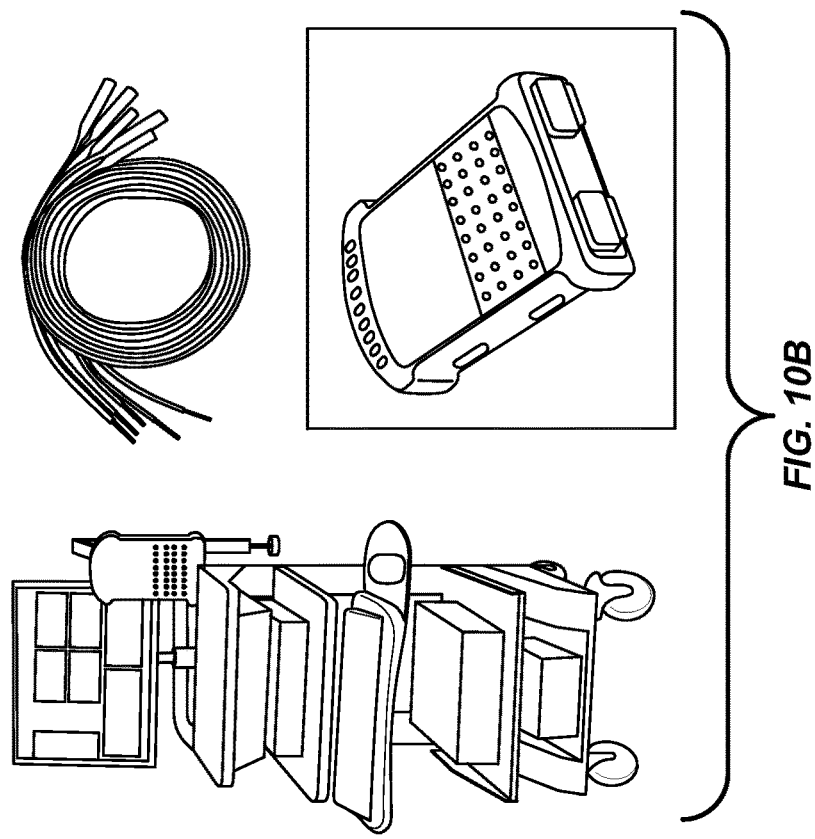
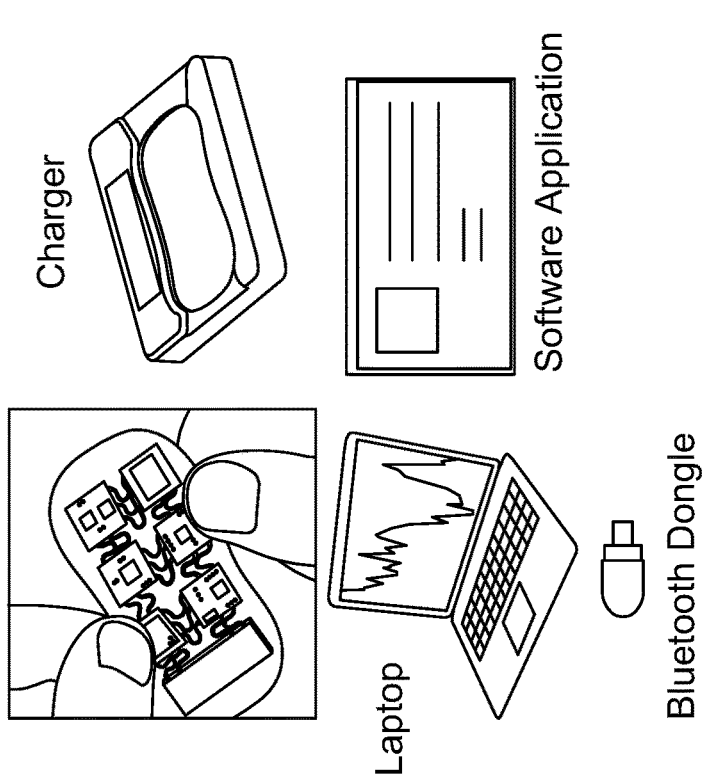
*FIG. 10B*
*FIG. 10A*

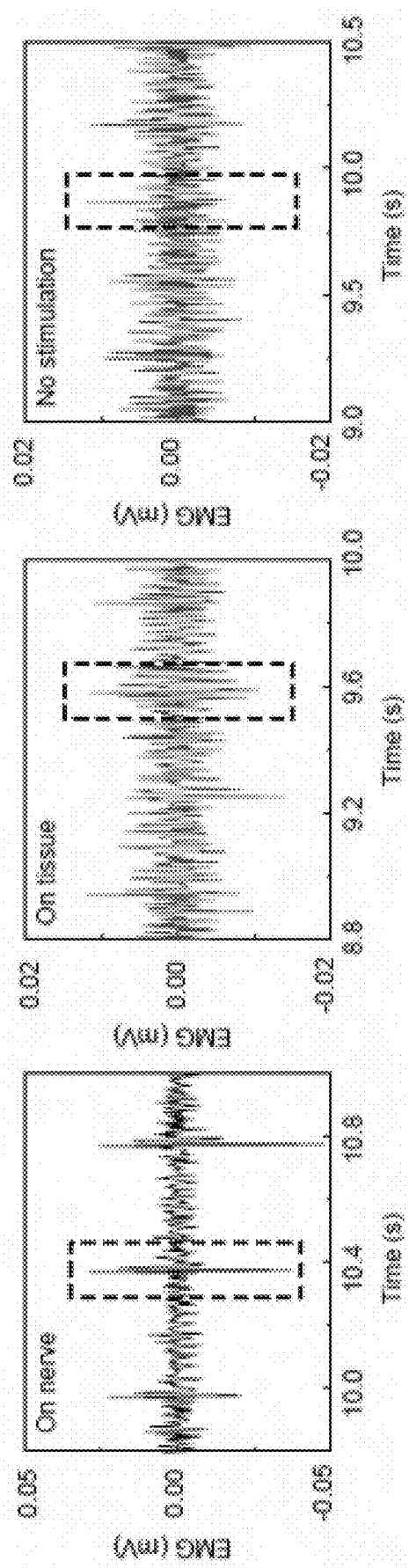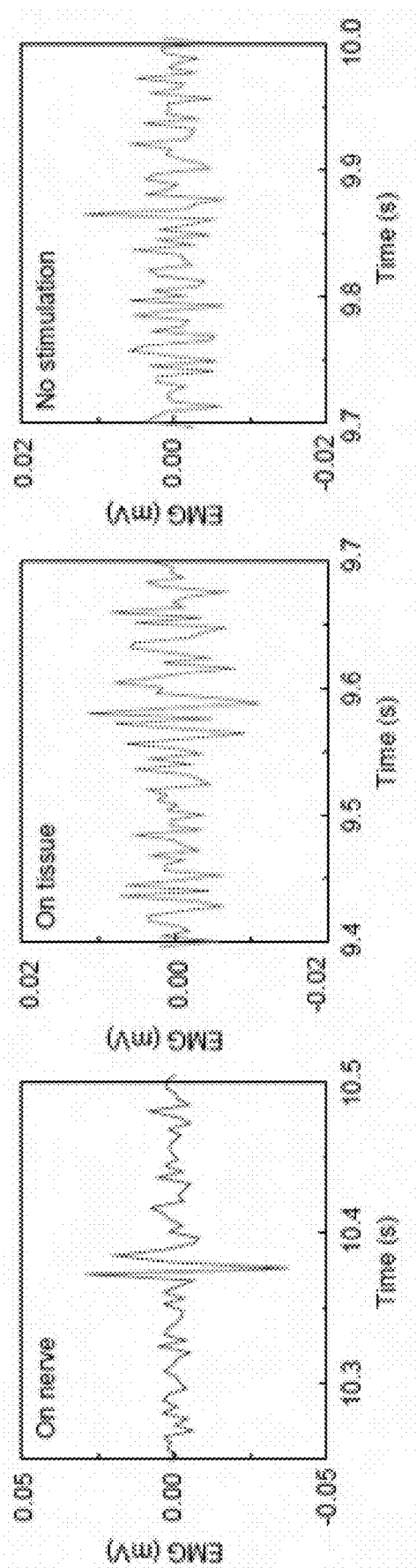
FIG. 12C FIG. 12B FIG. 12A FIG. 12F FIG. 12E FIG. 12D

INTRAOPERATIVE MONITORING OF NEUROMUSCULAR FUNCTION WITH SOFT, TISSUE-MOUNTED WIRELESS DEVICES

CROSS-REFERENCE TO RELATED APPLICATIONS

This application is a continuation application of U.S. patent application Ser. No. 16/969,649, filed Aug. 13, 2020, now allowed, which is a national stage entry of PCT Patent Application No. PCT/US2019/019166, filed Feb. 22, 2019, which itself claims claims the benefit of and priority to U.S. Provisional Patent Application No. 62/634,440, filed Feb. 23, 2018, which is hereby incorporated by reference in its entirety to the extent not inconsistent herewith.

BACKGROUND OF INVENTION

Surgical nerve damage where inadvertent damage is caused to nerves during surgery is a significant concern to medical professionals as it can lead to significant patient pain and, in some cases, loss of motor function. Intraoperative techniques have been developed to monitor nerve activity during surgery in attempts to avoid or reduce nerve damage. However, many conventional intraoperative techniques require that electrode leads be percutaneously placed inside of a patients muscle tissue and wired to a bench-top console, which causes patient discomfort and bleeding and requires additional surgery time and trained medical personnel, which increases costs. The increased cost of intraoperative monitoring has effectively limited its use to specific surgeries in which nerve damage is of high concern.

Nerve activity can be monitored using surface electromyography, removing the need for percutaneous electrode placement. Additionally, it has been suggested that wireless communication may be implemented to provide intraoperative monitoring of nerve activity, to provide medical practitioners critical feedback and help avoid nerve damage. For example, US Patent Publication No. 2006/0276702 describes the monitoring of nerve activity via electromyography using a wireless device. However, the described devices are relatively large and bulky, due to the requirement of additional components required for wireless transmission such as a transmitter, a battery, etc. The added size and rigidity of these components make them impractical for many surgeries as it is difficult to obtain or maintain conformal contact with tissue surface in order to provide accurate readings regarding nerve activity, and thus, their usefulness as an intraoperative monitoring system is limited.

It can be seen from the foregoing that there remains a need in the art for small, non-invasive, wireless sensors that are capable of conformal skin contact for intraoperative monitoring of surgical procedures to reduce nerve damage. Further, new microelectronic technologies may be implemented to reduce the number of components or reduce of the size of components, while increasing effectiveness.

SUMMARY OF THE INVENTION

The provided systems, methods and devices describe lightweight, wireless tissue monitoring devices that are capable of establishing conformal contact due to the flexibility or bendability of the device. The described systems and devices are useful, for example, for skin mounted intraoperative monitoring of nerve-muscle activity. The present systems and methods are versatile and may be used for a variety of tissues (e.g. skin, organs, muscles, nerves, etc.) to measure a variety of different parameters (e.g. electric signals, electric potentials, electromyography, movement, vibration, acoustic signals, response to various stimuli, etc.).

Advantageously, the present systems and methods take advantage of advances in microelectronics to reduce the size and rigidity of components allowing for soft, conformal devices. These devices may also be stretchable or bendable, without breaking or altering the functionality of the device. The described devices can be thin, soft and comfortable for the patient, while eliminating the need for wires which may be a nuisance for medical professionals during surgical procedures. The described devices may take advantage of various advancements in wireless technology such as Bluetooth and other near field communication techniques.

In an aspect, provided is a method of characterizing a neuromuscular property of a subject comprising: i) providing a conformable device comprising: a) a flexible or stretchable substrate; and b) a sensor supported by the flexible or stretchable substrate; the sensor comprising plurality of electrodes for measuring electric potentials of a tissue of the subject; wherein the flexible or stretchable substrate and sensor provide a net bending stiffness such that the device is capable of establishing conformal contact with a receiving surface of the tissue; ii) contacting the device with the receiving surface of the tissue, wherein contact results in the conformal contact of at least a portion of the device with the surface of the tissue; and iii) measuring a temporal profile of electric potentials of the tissue with the plurality of electrodes; thereby characterizing the neuromuscular property.

The described methods, systems and devices may provide a method or device for sensing, for example directly sensing, an electromyography signal or of the subject. The method may provide for sensing nerve conduction of the subject. The methods, systems, or devices may characterize various neuromuscular properties including, for example, threshold current to elicit an electromyography signal in response to electrical nerve stimulation and/or in a neuromuscular property is in response to electrical stimulation of the tissue, for example, direct electrical stimulation. The conformable devices may be capable of stretching, twisting or bending without altering functional operation and/or signal fidelity of the device.

The conformable device may comprise a plurality of sensors supported by the flexible or stretchable substrate, for example, each sensor independently comprising plurality of electrodes for measuring electric potentials of a tissue of the subject.

The neuromuscular property may be spontaneous muscle activity, for example activity corresponding to a level of anesthesia of the subject. This allows for the intraoperative monitoring of anesthesia to calculate the current level of anesthesia of a subject throughout an operation. The neuromuscular property may be depth of paralysis. Depth of paralysis may correspond to nerve or muscle activity of a tissue that has been treated with a paralytic agent.

The described methods, systems and devices are versatile and may incorporate a variety of sensors and sensing technologies. The described sensors can be electrical, thermal, mechanical or chemical in nature, for example, capable of measuring electric parameters, temperature, blood pressure, acoustics and various other sensing modalities. Further, the described devices may be useful with a variety of components and materials.

The present methods, systems and devices may measure a temporal profile of electric potentials to provide measurement of an electromyography (EMG) waveform. The methods, systems and devices may analyze the EMG waveforms. The temporal profile of electric potentials may provide a surface electromyography (s-EMG) measurement. The described electrodes may comprise at least a pair of Ag/AgCl electrodes or ENIG/AU electrodes. The sensor of the conformal device may be a multimodal sensor, providing for the sensing of a plurality of tissue properties. The present method may further comprise measuring one or more properties selected from the group consisting of tissue position, tissue movement, blood flow, blood pressure, a temperature, hydration state, tissue stiffness, mechano-acoustic signatures, and swelling.

The described sensor of the conformal device may further comprise a motion detector supported by the substrate, providing for measuring a temporal profile of the position, movement or both of the tissue. The motion detector may comprise an accelerometer, a gyroscope or both. The accelerometer or gyroscope may further characterize the neuromuscular property.

The described methods may further comprise: providing a stimulating conformal device comprising: a) a second flexible or stretchable substrate; b) an actuator for electrically stimulating the tissue of the subject, supported by the second flexible or stretchable substrate; and wherein the second flexible or stretchable substrate and the actuator provide a net bending stiffness such that the device is capable of establishing conformal contact with the receiving surface of the tissue; contacting the stimulating conformal device with the receiving surface of the tissue, wherein contact results in the conformal contact of at least a portion of the stimulating conformal device with the surface of the tissue; and stimulating the tissue using the actuator and simultaneously measuring a temporal profile of electric potentials of the tissue with the plurality of electrodes in response to the stimulation.

The methods and systems of stimulation described herein may occur internally (e.g. physically contacting a nerve within the tissue directly) or externally (e.g. stimulation through tissue, including skin, to stimulate underlying nerves.

The conformal device may comprise an actuator, which may provide stimulation of the tissue of the subject and the neuromuscular property may be in response to the stimulation, for example, electrical stimulation. The described methods may further comprise electrically stimulating the subject using the actuator and simultaneously measuring a temporal profile of electric potentials of the tissue with the plurality of electrodes in response to the electrical stimulation. The characterization of the neuromuscular property may be time-synced to the stimulation. The actuation may be electrical actuation, thermal actuation, acoustic actuation or any combination of these. The conformal device may further comprise a thermal actuator, which may provide thermal stimulation of the tissue of the subject.

The characterization of the neuromuscular property may trigger a downstream clinical response. The characterization of the neuromuscular property may provide a real-time clinical metric.

The sensor of the conformable device may have a stretchable or flexible island interconnect geometry. The stretchable or flexible island interconnect geometry may be characterized by a plurality of functional device components electrically interconnected via filamentary serpentine traces.

The provided methods, systems and devices eliminate the need for wires between the sensing device and console or data processing device. Additionally, wireless charging may reduce the size of the battery on the conformal device that is applied to the patient.

The described device may further comprise a one-way or two-way wireless component supported by the substrate and operationally connected to the sensor. The wireless component may be a wireless transmitter supported by the substrate, which may provide for outputting signals corresponding to the temporal profile of electric potentials. The wireless component may be a wireless receiver supported by the substrate; which may provide for receiving a signal from a user, a monitor or a device, for example, an additional conformable device as described herein or another separate device.

The device may further comprise a rechargeable battery providing power to the conformable device. The method may further comprise providing a monitor in wireless communication with one or more of the conformable devices. The method may further comprise displaying or audibly reporting the characteristic of the neuromuscular property, for example, to a doctor or medical professional. The monitor may be a smartphone, a laptop computer, a desktop computer, a tablet, a speaker, a wearable electronic or a console, which may establish a closed-loop feedback system for the doctor or medical professional to monitor nerve activity and adjust therapy accordingly.

One or more hydrogel layers may be provided between the tissue and the conformal device. The hydrogel may be a conductive gel. The described tissue may be an external tissue, for example, skin. The described tissue may be an internal tissue, for example, nervous system tissue. The tissue may be peripheral nerves, muscle, or spinal cord. A plurality of the conformal devices may be provided to a variety of receiving surface corresponding to tissues of the subject, which may provide for measuring a plurality of temporal profiles of electric potentials of the tissues, thereby characterizing the neuromuscular property.

The described method may use multiple devices to monitor muscle activities from multiple parts of a patient's body, including synchronized monitoring where the devices are time-synched to external or internal electrical stimulation, for example of peripheral nerves to promote recovery after surgery, or relevant surgical system. The methods described herein may further comprise a plurality of conformable devices, wherein the step contacting independently contacts each of the devices with one or more receiving surfaces of one or more tissues. The plurality of conformable devices may comprise: a) a conformable device capable of measuring an electrocardiogram; b) a conformable device capable of measuring an electrooculogram; and c) a conformable device capable of measuring an electromyogram. The plurality of conformable devices may be time-synched and may form a closed loop system.

The described systems, methods and devices may be capable of sensing very early signs of muscle reinnervation, for example, after a subject has undergone a surgical operation. The systems and methods described herein may detect muscle reinnervation or recovery at a very early stage, for example, prior to traditional methods of clinical detection such as muscle contraction.

In an aspect, provided is a conformable device comprising: i) a flexible or stretchable substrate; ii) a sensor supported by the flexible or stretchable substrate; the sensor comprising plurality of electrodes for measuring electric potentials of a tissue of the subject; and iii) a multilayer encapsulant at least partially encapsulating the sensor; the multilayer encapsulant comprising a lower modulus core layer at least partially embedding the sensor and a higher modulus shell at least partially surrounding the a first lower modulus core layer and sensor; wherein the lower modulus core layer has a Young's modulus at least 10 times lower than that of the higher modulus shell; wherein the flexible or stretchable substrate, sensor and multilayer encapsulant provide a net bending stiffness such that the device is capable of establishing conformal contact with a receiving surface of a tissue of a subject.

The device may be for measuring a temporal profile of electric potentials of the tissue; thereby characterizing a neuromuscular property of the subject. The lower modulus core layer may be characterized by an average Young's modulus equal to or less than 100 kPa, equal to or less than 50 kPa, or optionally, equal to or less than 10 kPa. The lower modulus core layer may be characterized by an average Young's modulus selected over the range of 1 kPa-100 kPa, selected over the range of 0.1 kPa-10 kPa, or optionally, selected over the range of 2 kPa-50 kPa. The lower modulus core layer may have an average thickness selected over the range of 2 microns to 2 millimeters, selected over the range of 2 microns to 1 millimeter, or optionally, selected over the range of 2 microns to 500 microns. The one or more hydrogel layers may contain pharmaceutical agents that are delivered upon skin contact, for example, delivered transdermally.

The higher modulus shell may be characterized by an average Young's modulus equal to or less than 2 MPa, equal to or less than 1 MPa, or optionally, equal to or less than 500 kPa. The higher modulus shell may be characterized by an average Young's modulus selected over the range of 50 kPa-2 MPa, selected over the range of 50 kPa-1 MPa, or optionally, selected over the range of 10 kPa-1 MPa. The higher modulus core layer may have an average thickness selected over the range of 10 microns to 2 millimeters, selected over the range of 10 microns to 1 millimeter, or optionally, selected over the range of 10 microns to 500 microns.

The lower modulus core layer may comprise a silicone composition. The higher modulus core layer may comprise a silicone composition. The lower modulus core layer and the higher modulus shell may combine to provide an effective modulus of the conformal device of less than or equal to 2 MPa, less than or equal to 1 MPa, or optionally, less than or equal to 500 kPa.

The described sensor may be a multimodal sensor. The sensor may further comprise one or more additional components for measuring one or more properties selected from the group consisting of tissue position, tissue movement, blood flow, blood pressure, a temperature, hydration state, tissue stiffness, mechano-acoustic signatures, and swelling. The sensor may further comprise a motion detector for measuring a temporal profile of the position, movement or both of the tissue. The motion detector may comprise an accelerometer, a gyroscope or both. The described electrodes may comprise at least a pair of Ag/AgCl electrodes or ENIG/AU electrodes.

The conformal device may further comprise an actuator for providing a stimulation of the tissue of the subject. The described stimulation may be electrical actuation, thermal actuation, acoustic actuation or any combination of these. The sensor of the conformable device may have a stretchable or flexible island interconnect geometry. The stretchable or flexible island interconnect geometry may be characterized by a plurality of functional device components electrically interconnected via filamentary serpentine traces.

The device may further comprise a one-way or two-way wireless component supported by the substrate and operationally connected to the sensor. The wireless component may be a wireless transmitter supported by the substrate for outputting signals corresponding to the temporal profile of electric potentials. The wireless component may be a wireless receiver supported by the substrate for receiving a signal from a user. The wireless component may be both a wireless transmitter and a wireless receiver.

The device may comprise one or more hydrogel layers, which may further comprise a conductive gel. The one or more hydrogel layers may characterized by an average thickness selected from the range of 0.1 millimeters to 2 millimeters, selected from the range of 0.1 millimeters to 1 millimeters, or optionally, selected from the range of 1 millimeters to 2 millimeters. The one or more hydrogel layers may be characterized by an average Young's modulus selected from the range of 1 kPa to 100 kPa, selected from the range of 1 kPa to 50 kPa, or optionally, selected from the range of 1 kPa to 250 kPa. The one or more hydrogel layers may be characterized by an electrical conductivity selected from the range of 0.1 S/m to 0.8 S/m, selected from the range of 0.3 S/m to 0.8 S/m, or optionally, selected from the range of 0.2 S/m to 1.0 S/m.

The devices, systems and methods may be used in an outpatient setting to help patients rehabilitate by sensing very early signs of muscle reinnervation, for example, after a surgical operation. This sensing may detect muscle reinnervation before obvious clinical signs of muscle contraction, providing biofeedback indicating subclinical signs of muscle reinnervation. The devices, systems and methods may perform studies similar to a convention EMG study.

In an aspect, provided is a system for characterizing a neuromuscular property of a subject comprising: i) one or more conformable devices each comprising: a) a flexible or stretchable substrate; b) a sensor supported by the flexible or stretchable substrate; the sensor comprising plurality of electrodes for measuring electric potentials of a tissue of the subject; and c) a multilayer encapsulant at least partially encapsulating the sensor; the multilayer encapsulant comprising a lower modulus core layer at least partially embedding the sensor and a higher modulus shell at least partially surrounding the a first lower modulus core layer and sensor; wherein the lower modulus core layer has a Young's modulus at least 10 times lower than that of the higher modulus shell; wherein the flexible or stretchable substrate, sensor and multilayer encapsulant provide a net bending stiffness such that the device is capable of establishing conformal contact with a receiving surface of a tissue of a subject; and ii) a monitor in wireless communication with the one or more conformable devices, wherein the receives data corresponding to the neuromuscular property of the subject from the one or more sensors and displays or audibly reports the neuromuscular property or changes in the neuromuscular property.

The system may comprise a plurality of conformable devices. The plurality of conformable devices comprise: a) a conformable device capable of measuring an electrocardiogram; b) a conformable device capable of measuring an electrooculogram; and c) a conformable device capable of measuring an electromyogram. The plurality of conformable devices may be time-synched and may form a closed-loop system.

The monitor may further comprise a processor and the monitor may analyze the data from one or more sensors. The monitor may be a smartphone, a laptop computer, a desktop computer, a tablet, a speaker, a wearable electronic or a console. The monitor may be in two-way communication with the one or more conformable devices to signal an actuator in the one more conformable devices.

The monitor may display the neuromuscular property, thereby providing a real-time clinical metric. The real-time clinical metric may trigger a downstream clinical response.

In an aspect, provided is a method of monitoring a level of anesthesia of a subject comprising: i) providing a conformable device comprising: a) a flexible or stretchable substrate; and b) a sensor supported by the flexible or stretchable substrate; the sensor comprising plurality of electrodes for measuring electric potentials of a tissue of the subject; wherein the flexible or stretchable substrate and sensor provide a net bending stiffness such that the device is capable of establishing conformal contact with a receiving surface of the tissue; ii) contacting the device with the receiving surface of the tissue, wherein contact results in the conformal contact of at least a portion of the device with the surface of the tissue; iii) measuring a temporal profile of electric potentials of the tissue with the plurality of electrodes corresponding to spontaneous muscle activity; and iv) monitoring the spontaneous muscle activity in real time during an operation, wherein the spontaneous muscle activity corresponds to the level of anesthesia of the subject.

Monitoring the level of anesthesia of the subject may comprise treating the subject with a paralytic agent to prevent spontaneous movement of the tissue; wherein the step of monitoring spontaneous muscle activity further comprises monitoring a depth of a paralysis of the tissue.

Monitoring the spontaneous muscle activity or the level of anesthesia may provide a real-time clinical metric. The real-time clinical metric may trigger a downstream clinical response.

In an aspect, provided is a method of promoting nerve recovery of a subject comprising: i) providing a sensing conformable device comprising: a) a flexible or stretchable substrate; b) a sensor supported by the flexible or stretchable substrate; the sensor comprising plurality of electrodes for measuring electric potentials of a tissue of the subject; and wherein the flexible or stretchable substrate and sensor provide a net bending stiffness such that the device is capable of establishing conformal contact with a receiving surface of the tissue; ii) providing a stimulating conformable device comprising: a) a second flexible or stretchable substrate; an actuator for stimulating the tissue of the subject, supported by the second flexible or stretchable substrate; and wherein the second flexible or stretchable substrate and the actuator provide a net bending stiffness such that the device is capable of establishing conformal contact with the receiving surface of the tissue; iii) contacting the flexible device and the stimulating conformal device with the receiving surface of the tissue, wherein contact results in the conformal contact of at least a portion of the flexible device and the stimulating conformal device with the surface of the tissue; and iv) stimulating the tissue using the actuator and simultaneously measuring a neuromuscular property is in response to the stimulation, wherein stimulation of the tissue promotes nerve recovery in the tissue.

Nerve recovery may be axonal regeneration, inhibition of demyelination, promotion of remyelination, secretion of trophic factors or a combination thereof. Actuation may be, for example, electrical actuation, thermal actuation, acoustic actuation or any combination of these.

In an aspect, the invention provides methods or systems for intraoperative monitoring, therapy or both. In an aspect, the invention provides methods or systems for postoperative monitoring, therapy or both. In an aspect, the invention provides methods or systems for preoperative monitoring, therapy or both.

In an aspect provided is a method of characterizing a neuromuscular property of a subject comprising: i) providing a conformable device comprising: a flexible or stretchable substrate; at least one actuator for providing electrical stimulation; and a sensor supported by the flexible or stretchable substrate; the sensor comprising plurality of electrodes; wherein the flexible or stretchable substrate and sensor provide a net bending stiffness such that the device is capable of establishing conformal contact with a receiving surface of a tissue of the subject; ii) contacting the device with the receiving surface of the tissue, wherein contact results in the conformal contact of at least a portion of the device with the surface of the tissue; iii) establishing electrical communication between the actuator and a nerve of the subject, wherein the contact is established by internal contact of the actuator with the nerve of the subject, by external contact of the actuator with the tissue of the subject or a combination thereof; and iv) stimulating the nerve via the actuator and measuring a temporal profile of electric potentials of the tissue or the nerve with the plurality of electrodes; thereby characterizing the neuromuscular property. Any of described methods and devices may be use for monitoring and confirming effective electrical stimulation of the tissue or the nerve.

In an aspect, provided is a method of detecting muscle reinnervation of a subject comprising: i) providing a conformable device comprising: a flexible or stretchable substrate; and a sensor supported by the flexible or stretchable substrate; the sensor comprising plurality of electrodes for measuring electric potentials of a tissue of the subject; wherein the flexible or stretchable substrate and sensor provide a net bending stiffness such that the device is capable of establishing conformal contact with a receiving surface of the tissue; ii) contacting the device with the receiving surface of the tissue, wherein contact results in the conformal contact of at least a portion of the device with the surface of the tissue; and iii) measuring a temporal profile of electric potentials of the tissue with the plurality of electrodes; thereby characterizing the muscle reinnervation.

Any of the conformable devices described herein may be capable of detecting muscle reinnervation prior to clinical detection and/or prior to muscle contraction. The described methods and systems may be post-operative.

As described herein and applied any of the described methods, system and devices, conformal contact may involve direct physical contact between one or more contact surfaces of the device and said receiving surface of the tissue. Conformal contact may involve indirect contact between one or more contact surfaces of the device and said receiving surface of the tissue. Conformal contact may involves direct physical contact or indirect contact between one or more contact surfaces of the device and said receiving surface of a surface of a skin of a subject. Conformal contact may involve direct physical contact or indirect contact between one or more contact surfaces of the device and said receiving surface of an internal tissue of a subject, for example, internal tissue may be peripheral nerves, muscle, or spinal cord tissue.

Without wishing to be bound by any particular theory, there may be discussion herein of beliefs or understandings of underlying principles relating to the devices and methods disclosed herein. It is recognized that regardless of the

BRIEF DESCRIPTION OF THE DRAWINGS

FIG. 1A Exploded view schematic illustration of the key mechanical and electrical components of the system. FIG. 1B Illustration of the conformable device fully assembled and encapsulated with soft elastomeric materials. FIG. 1C conformable device held in stretched, twisted and bent geometries. FIG. 1D Simplified cross-sectional schematic of the electronics, core and shell encapsulation layers. FIG. 1E Computational results for interfacial stresses exerted on the skin in response to 20% tensile stretch. The shear and normal stresses vary with the thickness of the core layer ($h_{core}$: 0.5 mm, 1.5 mm, 2.5 mm). FIG. 1F Spatial distribution of strain in the circuit components for different levels of uniaxial stretching, for different values of $h_{core}$.

FIGS. 2A-2D. Comparative analysis of EMG recordings captured using a conformable device and standard neurophysiological monitoring equipment. FIG. 2A Anatomical placement of the conformable device, surface electrodes, and needle electrodes on the tibialis anterior muscle. FIG. 2B Surgical access site exposing the common peroneal nerve. FIG. 2C Comparison of stimulation current thresholds for the three monitoring systems determined using the configuration shown in FIG. 2A. FIG. 2D Motion and EMG waveforms recorded with the conformable device during direct nerve stimulation.

FIGS. 3A-3H. Comparison of the quality of EMG signal from the tibialis anterior muscle group captured using the conformable device and conventional equipment (needle electrodes and standard recording electronics) during stimulation of the common peroneal nerve. FIG. 3A Average current thresholds determined using the conformable device and conventional equipment in response to stimulation of the peroneal nerve (n=10 patients). FIG. 3B Bland-Alman analysis of the conformable device and conventional equipment (needle, n=55 subjects) showing data sets falling within +0.18 mA (upper limit: UL) and −0.15 mA (lower limit: LL). FIG. 3C and FIG. 3D EMG signals captured using the conformable device and conventional equipment, respectively for different stimulation currents with patient 1. FIG. 3E Signal-to-noise ratio (SNR) of EMG signals shown in FIG. 3C and FIG. 3D. FIGS. 3F-3H show similar data for patient 2. For parts FIGS. 3C-3D and FIGS. 3F-3G EMG amplitudes (y-axis) correspond to normalized values.

FIG. 4A Anatomical placement of the conformable device and needle electrodes on the left tibialis anterior muscle. FIG. 4B Surgical access site for direct stimulation of exposed left L5 spinal nerve. EMG signals were captured on the left anterior tibialis muscle. FIG. 4C Average current thresholds for the conformable device and conventional equipment derived from EMG signals from the tibialis anterior muscle. FIG. 4D Anatomical placement of the conformable device and needle electrodes on the left facial muscle. FIG. 4E Surgical access site for direct stimulation of the exposed facial nerve. FIG. 4F Average current thresholds for the conformable device and conventional equipment derived from EMG signals from the left facial muscle.

FIG. 5C Stress-strain curves measured by fixing both ends of the conformable device (not by the ends of the package) for FIG. 5A core/shell and FIG. 5B standard designs. The effective moduli are 390 kPa and 890 kPa for the core/shell and standard designs, respectively.

FIG. 6A Schematic cross sectional illustration of the conformable device in an undeformed state. FIG. 6B The conformable device undergoing bending to a defined curvature, a.

FIGS. 10A-10B. Comparison of the components of the conformable device described herein and the Cadwell® Cascade® monitoring system. FIG. 10A Example conformable device prototype device (top left), charging station (top right), laptop workstation with Bluetooth connection running a custom software application (bottom) to capture and visualize data streamed wirelessly from the device. FIG. 10B Cadwell® Cascade® operating station (left), needle electrodes with standard cable length (top right), and 16-channel adapters for electrode connections (bottom right).

FIGS. 12A-12F. Effect of stimulation artifacts on the conformable device s-EMG signals. Measured s-EMG response of conformable device positioned at the tibialis anterior muscle in response to direct current simulation applied to FIG. 12A right leg tibial nerve, FIG. 12B nearby tissue, and with FIG. 12C no stimulation applied when the electrode was placed on the nerve. Magnified view of s-EMG waveforms shows distinguishable features of s-EMG in response to stimulation FIG. 12D on nerve, FIG. 12E on surrounding tissue, and FIG. 12F without stimulation.

FIG. 13A Conformable device EMG signal response as a function of direct nerve stimulation current level. FIG. 13B Commercial monitoring system with needle electrode signal response with increased direct nerve stimulation current, served as a reference to FIG. 13A. FIG. 13C The signal-to-noise ratio of EMG signal response as a function of direct nerve stimulation current level in FIG. 13A and FIG. 13B.

DETAILED DESCRIPTION OF THE INVENTION

Figure 1B:
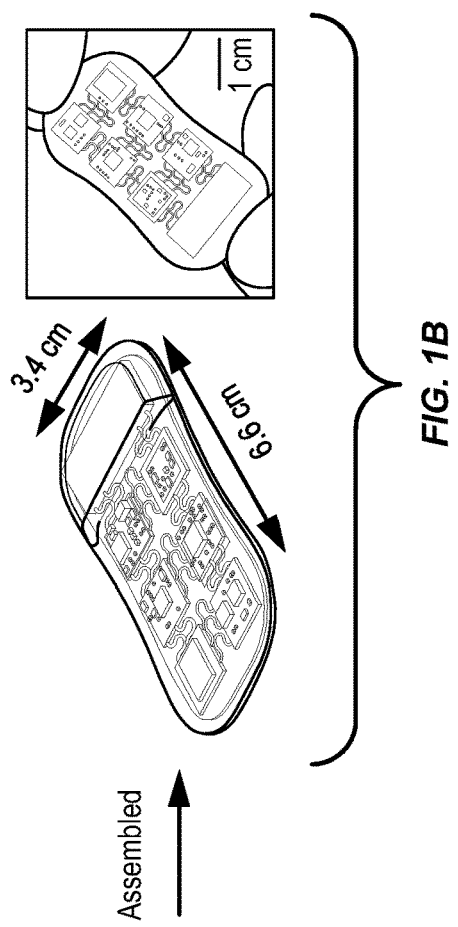
FIGS. 1A-1F. Wearable biosensing system in a soft, stretchable design.

In general, the terms and phrases used herein have their art-recognized meaning, which can be found by reference to standard texts, journal references and contexts known to those skilled in the art. The following definitions are provided to clarify their specific use in the context of the invention.

"Neuromuscular property" refers to a property or a condition of a tissue of a patient, for example, the skin, a muscle or a nerve. For example, a property may relate to the electric potential of the tissue such as an electric potential, an electric current or an electromyography (EMG) signal. Neuromuscular property may refer to conditions of the tissue, such as position, stiffness, movement or hydration state of the tissue. Neuromuscular properties may also include properties relating to blood flow within the tissue, such as blood pressure, blood flow or swelling. Neuromuscular property may include, for example, spontaneous muscle activity which may be useful monitoring the level of anesthesia currently being experienced by a tissue or nerve. Neuromuscular property may be the level of paralysis if the tissue has been treated with a paralytic agent.

"Substrate" refers to a device component, such as a layer, having a surface that is capable of supporting, accommodating, embedding or otherwise integrating a structure, including a sensor, an actuator, a microfluidic structure, optical structure, electronic structure, thermal structure or any combination of these. Substrates in some embodiments are capable of supporting, accommodating, embedding or otherwise integrating a device component such as conformal device component. In some embodiments, a substrate is capable of at least partially forming an interface with the tissue of a subject, such as with the epidermis or other organ of a subject. In an embodiment, a substrate of the present devices, systems and methods is a biocompatible and/or bioinert material. In an embodiment, a substrate of the present devices, systems and methods is a polymer or elastomer material. Substrates of the invention include "functional substrates" which refers to a substrate component for a device having at least one function or purpose in addition to providing mechanical support for a component(s) disposed on or within the substrate such as a microfluidic functionality, a mechanical functionality, optical functionality or a thermal functionality. A functional substrate may facilitate mechanical, thermal, chemical and/or electrical matching of the functional substrate and the skin of a subject such that the mechanical, thermal, chemical and/or electrical properties of the functional substrate and the skin are within 20%, or 15%, or 10%, or 5% of one another. Devices and systems of the invention may have more than one substrate, for example, such as embodiments having a lower modulus core layer and a high modulus shell. In some embodiments, the lower modulus core layer is provided in conformal contact with a tissue, for example, the skin. For example, the invention includes devices and systems having a stretchable or flexible island interconnect geometry, which is shown in FIG. 1.

In some embodiments, a substrate is mechanically matched to a tissue, such as mechanically matched to skin. In an embodiment, a mechanically matched substrate is optionally capable of providing an interface for establishing fluid communication and/or conformal contact with a surface of the tissue, such as skin. Devices and methods of certain embodiments incorporate substrates comprising soft materials, for example exhibiting flexibility and/or stretchability, such as polymeric and/or elastomeric materials. In an embodiment, a mechanically matched substrate has a modulus less than or equal to 100 MPa, and optionally for some embodiments less than or equal to 10 MPa, and optionally for some embodiments, less than or equal to 1 MPa. In an embodiment, a mechanically matched substrate has a thickness less than or equal to 0.5 mm, and optionally for some embodiments, less than or equal to 1 cm, and optionally for some embodiments, less than or equal to 3 mm. In an embodiment, a mechanically matched substrate has a bending stiffness less than or equal to 1 nN m, optionally less than or equal to 0.5 nN m.

"Conformable" refers to a device, material or substrate which has a bending stiffness that is sufficiently low to allow the device, material or substrate to adopt a desired contour profile, for example a contour profile allowing for conformal contact with a surface characterized by a surface topography comprising recessed and/or relief features. In certain embodiments, a desired contour profile is that of tissue, such as skin.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of 70% or more of the of the surface area of one or more contact surfaces of the device to the shape of the receiving surface of a subject, optionally 90% or more of the of the surface area of one or more contact surfaces of the device to the shape of the receiving surface of a subject and optionally 95% or more of the of the surface area of one or more contact surfaces of the device to the shape of the receiving surface of a subject In an embodiment, conformal contact involves adaptation of a contact surface(s) of the device to a receiving surface(s) such that intimate contact is achieved, for example, wherein less than 20% of the surface area of a contact surface of the device does not adapt to the shape of (and optionally does not physically contact) the receiving surface, or optionally less than 10% of a contact surface of the device does adapt to the shape of (and optionally does not physically contact the receiving surface), or optionally less than 5% of a contact surface of the device does not adapt to the shape of (and optionally does not physically contact) the receiving surface. In some embodiments, devices of the invention are capable of establishing conformal contact, and optionally physical contact, with external tissue of a subject, such as a portion of the skin of a subject or internal tissue of a subject, such as peripheral nerves, muscle, or spinal cord. Conformal contact may refer to contact between the device and receiving surface which places the device in operable electrical communication with the skin or underlying nerves or muscles to allow for the sensing or actuation of the tissue or nerve. Conformal contact may be achieved by establishing direct physical contact between the surface area of one or more contact surfaces of the device and the receiving surface of a subject. Alternatively, conformal contact may be achieved by establishing indirect contact between the surface area of one or more contact surfaces of the device and the receiving surface of a subject, for example, indirect contact characterized by one or more intermediate structures or materials, such as an adhesive, bonding or therapeutic layer or material, provided between the one or more contact surfaces of the device and the receiving surface of a subject.

"Sensing" refers to an action of detecting the presence, absence, amount, magnitude and/or intensity of one or more physical and/or chemical properties or characteristics. Sensor refers to a device or component thereof that is capable of sensing. Useful device components for sensing include, but are not limited to electrode elements, chemical or biological sensor elements, acoustic sensors, pressure sensors, electrochemical sensors, temperature sensors, strain sensors, mechanical sensors, position sensors, optical sensors and capacitive sensors.

"Sensor" refers to a device component useful as a sensor and/or useful for detecting the presence, absence, amount, magnitude or intensity of a physical property, object, radiation and/or chemical. Sensors in some embodiments function to transduce a biological signal into an electrical signal, optical signal, wireless signal, acoustic signal, etc. Useful sensing elements include, but are not limited to electrode elements, chemical or biological sensor elements, pH sensors, optical sensors, photodiodes, temperature sensors, capacitive sensors strain sensors, acceleration sensors, movement sensors, displacement sensors, pressure sensors, acoustic sensors or combinations of these. Particularly useful sensors are those that measure electrical potential or pressure (or force, such as by the equation Pressure=Force divided by the area over which the force is measured, so that a measure of one of pressure or force allows the other to be calculated, with the area generally corresponding to the sensor area) or temperature. The devices described herein may be multi-modal, with multiple different sensor types to provide simultaneous measure of multiple different physiological parameters, such as temperature and pressure.

"Stimulating" or "Actuating" refers to an action of acting on, stimulating, controlling, or otherwise affecting a structure, material or device component. Actuator refers to a device or component thereof that is capable of stimulating or actuating. Useful device components for actuating or stimulating include, but are not limited to, electrode elements, electromagnetic radiation emitting elements, light emitting diodes, lasers, magnetic elements, acoustic elements, piezoelectric elements, chemical elements, biological elements, and heating elements.

"Actuator" refers to a device component useful for interacting with, stimulating, controlling, or otherwise affecting an external structure, material or fluid, for example a biological tissue. Useful actuating elements of the actuator include, but are not limited to, electrode elements, electromagnetic radiation emitting elements, light emitting diodes, lasers, magnets in an oscillating magnetic field, chemical or biological release agents, and heating elements. Actuators include electrodes for providing a voltage or current to a tissue, heaters for providing heat to a tissue, mechanical actuators for generating force or pressure to a tissue. Actuators may include sources of electromagnetic radiation for providing electromagnetic radiation to a tissue. Actuators include thermal sources for heating tissue. Actuators include displacement sources for displacing or otherwise moving a tissue.

The terms "flexible" and "bendable" are used synonymously in the present description and refer to the ability of a material, structure, device or device component to be deformed into a curved or bent shape without undergoing a transformation that introduces significant strain, such as strain characterizing the failure point of a material, structure, device or device component. In an exemplary embodiment, a flexible material, structure, device or device component may be deformed into a curved shape without introducing strain larger than or equal to 5%, for some applications larger than or equal to 1%, and for yet other applications larger than or equal to 0.5% in strain-sensitive regions. A used herein, some, but not necessarily all, flexible structures are also stretchable. A variety of properties provide flexible structures (e.g., device components) of the invention, including materials properties such as a low modulus, bending stiffness and flexural rigidity; physical dimensions such as small average thickness (e.g., less than 10000 microns, optionally less than 1000 microns and optionally less than 100 micron) and device geometries such as thin film and mesh geometries.

"Stretchable" refers to the ability of a material, structure, device or device component to be strained without undergoing fracture. In an exemplary embodiment, a stretchable material, structure, device or device component may undergo strain larger than 0.5% without fracturing, for some applications strain larger than 1% without fracturing and for yet other applications strain larger than 3% without fracturing. A used herein, stretchable structures may also be flexible. Some stretchable structures (e.g., device components) are engineered to be able to undergo compression, elongation and/or twisting so as to be able to deform (and optionally operate) without fracturing. Stretchable structures include structures comprising stretchable materials, such as elastomers; and bent, coiled or serpentine structures capable of elongation, compression and/or twisting motion.

"Wireless controller" refers to electronic components, including chips, that provide for wireless control of the sensors or actuators. Similarly, "wirelessly transmitter" refers to electronic components, including chips, for transmitting data to an external reader. An example of such wireless components is a Bluetooth communication chip or a near field communication (NFC) chip, including NFC chips from Texas Instruments. NFC is a radio technology enabling bi-directional short range wireless communication between devices. In this manner, a controller external to the actuator device (e.g., off-circuit) can be used to provide actuator control and to receive information from the actuator device, including device status or information from one or more on-circuit sensors.

"Power harvesting" refers to a process by which energy is derived from an external source and, thereby, may avoid the need for relatively large, bulky and expensive primary or secondary battery systems. Of course, the devices provided herein may be compatible with batteries, depending on the application of interest. For example, relatively heavy or bulky systems may be incorporated into clothing, shoes, hats, gloves, scarves, face masks, and the like, in a manner that would be unobtrusive, or minimally noticeable, to a user.

In this fashion, the devices provided herein are capable of "wirelessly operation", without a need for hard-wiring to a receiver for control, powering, transmitting or communication.

Adjacent" to the biological surface or to the skin refers to positioning the device so that the sensor may reliably measure a physiological parameter associated with the underlying biological material. The sensor may measure a parameter of interest on the skin or beneath the skin, such as blood flow, oxygen level, temperature, pressure, optical parameter, tissue stiffness, moisture level, or the like. Accordingly, a device may be considered adjacent if it is directly mounted to the surface, or has an intervening layer, including an adhesive and/or barrier layer, so long as the functionality of the actuator or sensor is maintained. Adjacent may also be described as within 1 mm, 500 µm, 100 µm, 10 µm or 1 µm of the skin surface.

"Real-time clinical metric" is used broadly herein to refer to any output that is useful in providing a clinician or operator information on a subject's medical well-being. It may be useful in understanding or training a biological function. It may refer to a neuromuscular property, a level of anesthesia of a subject, a level of paralysis of a tissue that has been treated with a paralytic agent, or the promotion of nerve recovery.

"Nerve recovery" as used broadly herein refers to a positive change or condition or health of a nerve, a group of nerves or a nervous system. Nerve recovery may refer to, for example, axonal regeneration of a nerve, inhibition of demyelination or promotion of remyelination. Nerve recovery may also refer to inducing secretion of a trophic factor by the subject.

"Operably connected" refers to a configuration of elements, wherein an action or reaction of one element affects another element, but in a manner that preserves each element's functionality. For example, a wireless controller such as an NFC chip operably connected to a sensor refers to the ability to power the sensor and communicate with an external data reader without impacting the functionality of the sensor.

Example 1: Intraoperative Monitoring of Neuromuscular Function with Soft, Skin Mounted Wireless Devices Abstract Peripheral nerves are often vulnerable to damage during surgeries, with risks of significant pain, loss of motor function and reduced quality of life for the patient. Intraoperative methods for monitoring nerve activity are effective, but conventional systems rely on bench-top data acquisition tools with hard-wired connections to electrode leads that must be placed percutaneously inside target muscle tissue. These approaches are time and skill intensive and therefore costly, to an extent that precludes their use in many important scenarios. Described herein is a soft, skin-mounted monitoring system that measures, stores and wirelessly transmits electrical signals and physical movement associated with muscle activity, continuously and in real-time during neurosurgical procedures on the peripheral, spinal, and cranial nerves. Surface electromyography and motion measurements can be performed non-invasively in this manner on nearly any muscle location, thereby offering many important advantages in usability and cost, with signal fidelity that matches that of the current clinical standard of care. These results could significantly improve accessibility of intraoperative monitoring across a broad range of neurosurgical procedures, with associated enhancements in patient outcomes.

INTRODUCTION

Injuries to peripheral nerves during surgical procedures constitute a significant source of morbidity and result in worsened quality of life for many patients. Iatrogenic peripheral nerve damage is a particularly common and devastating clinical entity that leads to significant pain and compromised functional outcomes. For example, approximately 5% of patients undergoing arthroscopic hip repair suffer from transient neuropraxia. Permanent damage to nerves is a well-known and debilitating health risk associated with peripheral, cranial and spinal nerve access. In such cases, intraoperative monitoring techniques, primarily involving evoked potentials as well as stimulated and spontaneous electromyography (EMG), provide surgeons with the ability to identify and assess vulnerable nerve sites by probing nerve-muscle activities during surgery. Real-time monitoring strategies offer a powerful set of capabilities for surgeons that can positively affect outcomes, but existing intraoperative systems are large, expensive and cumbersome; they include data acquisition consoles coupled to sensing electrode leads via multiple, fixed electrical connections. These platforms demand active engagement of trained technicians who are skilled in their operation and in the placement of needle electrodes, thus preventing access to neurosurgical care in settings where such tools are unavailable and/or where the associated costs cannot be supported. Furthermore, the wired interfaces create spatial complexity and limit electrode placement and the needle electrodes used for recording EMG signals cause discomfort due to penetration through the dermis, commonly leading to postoperative pain and/or soft tissue hematomas. The quality of the EMG signals also depends critically on precise placement of these needles. This set of clinical limitations establishes a clear need for alternative intraoperative monitoring approaches.

Described herein is a system utilizing multimodal measurement modalities and high signal quality, but in physical formats and functional designs that provide: 1) soft and conformal tissue interfaces compatible with skin across all regions of the body, 2) wireless communication capabilities and on-board power supplies capable of supporting operation continuously during an entire surgical procedure, 3) non-invasive electrodes that interface with the skin, without requiring penetration, specialized skin preparation procedures or precise spatial positioning, 4) easy-to-use interfaces with automated data capture, storage and real-time analysis, and 5) path to low-cost embodiments. Here, we present a thin, soft biosensing device, referred to as 'conformable device', and demonstrate the utility of its unique features during intraoperative neurosurgical monitoring. The soft mechanical construction and advanced encapsulation strategies allow the use of the conformable device prototype across a broad range of neurosurgical procedures, which has not been demonstrated previously. Furthermore, the soft system-level mechanics enable intimate mechanical coupling of the conformable device to the skin, even on sensitive curvilinear regions of the face, where it can capture electrical activity (e.g. EMG) and movement of targeted muscle groups in response to direct electrical stimulation of nerves, in real-time during critical interventional procedures. Detailed clinical studies on multiple patients establish the performance characteristics and practical advantages of this technology relative to conventional needle and surface-EMG (s-EMG) measurement techniques during surgeries on peripheral, spinal and cranial nerves.

Experimental Section
Materials and Methods.
Design of Clinical Study

This study was approved by the Northwestern University's Investigational Review Board (IRB #: STU00201505) and consents were obtained from all patients prior to undergoing surgery and the scientific research study. All patients were administered general anesthesia without long-lasting paralytic agents so that muscle activity could be monitored. Once anesthetized, the conformable devices were placed on the skin overlying relevant muscles that were also being monitored using standard needle EMG techniques. In several patients, conventional s-EMG electrodes were also used. Nerve-muscle activities were measured once target nerves were exposed surgically and direct current stimulation could be applied, as instructed and overseen by the main surgeon.

Conventional EMG Sensing Electrodes and Stimulation

Figure 11B:
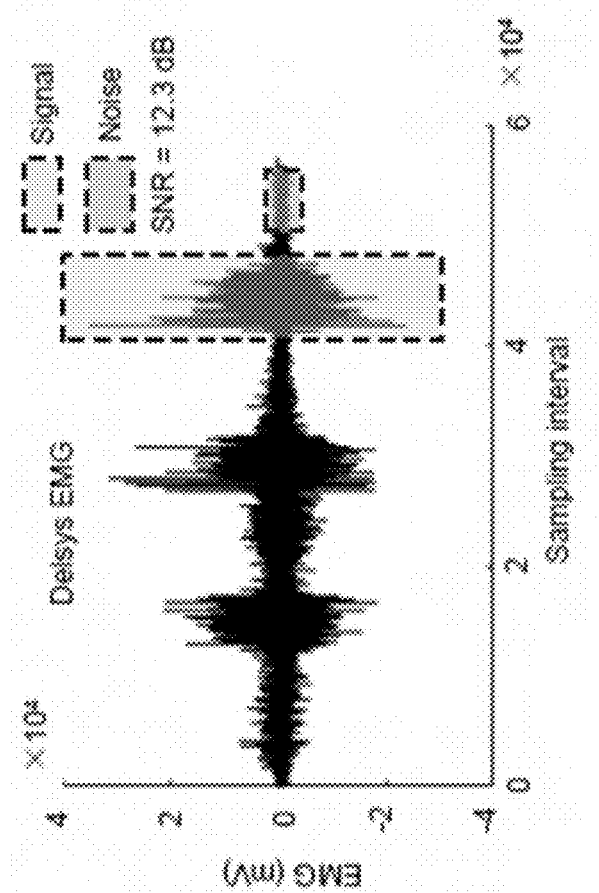
FIGS. 11A-11B. Comparison of fidelity of signals captured using the conformable device and Delsys s-EMG system. s-EMG waveforms from FIG. 11A conformable device and FIG. 11B Delsys system during flexion of thigh muscles. Baseline noise (at rest) is indicated for both systems. SNR estimates are comparable for the described conformable device (~12.5 dB) and Delsys (~12.3 dB).
Figure 11A:
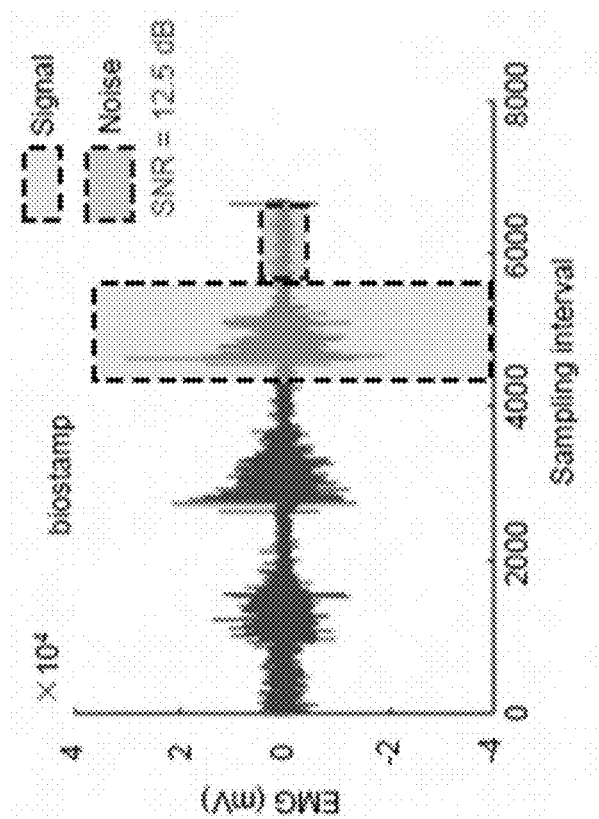

Needle electrodes (Rhythmlink, 13-mm long, 0.4-mm diameter, 1.5-m leadwire, SP119022, stainless steel) served to monitor nerve activity during the surgeries. A stimulation probe delivered direct current to the targeted site (Prass Standard Flush-Tip Probe, Medtronic Xomed, ~10-cm long, stainless steel with plastic handle). The electrodes electrically connected to an external stimulator box (Cadwell® Cascade® IONM System). The stimulation pulses consisted of monophasic waveforms (at 2.6 Hz, 200 µs pulse width), at adjustable current levels with control at the level of 0.01 µA. The s-EMG recordings used hydrogel adhesive electrodes with Ag/AgCl backing layer (AMBU/Neuroline Surface Electrodes, Disposable, 700 SERIES). The distance between electrodes on the conformable device was ~5 cm. The needle and s-EMG electrodes were positioned ~5 cm apart, next to the conformable device, to facilitate comparison. The details of the data acquisition system and noise floor for the s-EMG electrodes and the needle electrodes can be found in the Table 51 and FIG. 11.

Figure 14:
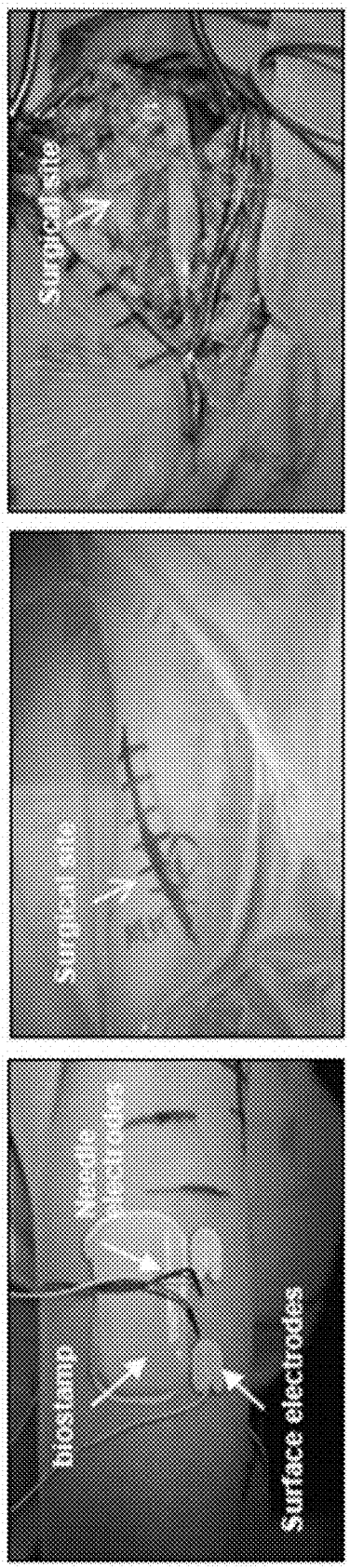
FIG. 14. Nerve-muscle study procedure of patient 1 to non-invasively monitor muscle-nerve activity (using conformable device as described herein), surgically access and electrically stimulate nerves while capturing s-EMG recordings from muscles.
Figure 14:
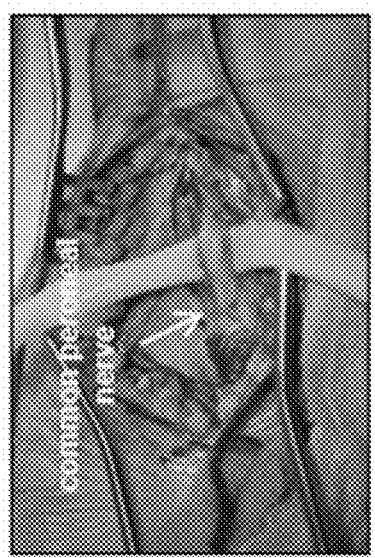

Surgery to Expose and Electrically Stimulate Nerves while Recording from Muscles The skin overlying the nerve was infiltrated superficially with local anesthetic and epinephrine. The peripheral nerve was then exposed using standard surgical techniques. Once exposed, a monopolar electrical nerve stimulation device (Prass Standard Flush-Tip Probe, Medtronic Xomed) applied electrical current at different threshold levels either directly to the surface of the nerve or to the surrounding tissues as a control (FIG. 14).

Stimulation Current Threshold Study

To define the thresholds, electrical stimulation was directly applied to the surface tissues of the nerve. The stimulus starts at electrical current levels that are too low to elicit activity in the studied muscle as measured by conventional EMG monitoring system. The stimulus level is then increased gradually until a muscle response could be recorded using the conformable device and the conventional intraoperative monitoring system (Cadwell® Cascade® IONM Pro) (FIG. 11) separately. A trained intraoperative monitoring specialist at Northwestern Memorial Hospital determined the threshold current value at the point when the EMG signal waveform was visually distinguishable. This procedure was repeated six times and the stimulus threshold level for eliciting a detectable muscle response was recorded during each trial. The data were collected and then analyzed postoperatively. The reported values correspond to the average of six trials with one standard deviation as error bars.

Signal Recording

Needle electrode and s-EMG signals were recorded using the Cadwell® Cascade® IONM system under Free Run EMG mode. The built-in ADC has a sampling rate of 25.6 kHz at a gain of 50 µV/div at 18-bit resolution. The detected EMG signal was time-locked to the applied stimulation pulses. Conformable device s-EMG signals were collected with a custom engineering app interface with a sampling rate of 250 Hz and gain of 12 at 16-bit resolution.

Signal Processing

All needle and surface EMG signals were exported from the Cadwell® Cascade® IONM system without any data processing. Conformable device EMG signals were processed with a high pass $7^{TH}$ order Butterworth filter at 25 Hz. Time scales were manually aligned to synchronize the onset of nerve-muscle response from direct electrical stimulation. The SNR in dB scale is defined as 10 times $\log_{10}$ (Variance$^2_{signal}$/Variance$^2_{Noise}$) for a set period of time. All data were processed using Origin Pro software.

Mechanical Modeling and Finite Element Analysis

Three-dimensional finite element analysis (FEA) simulations based on commercial software packages (ABAQUS) guided optimization of the mechanics of the system. The flexible circuit model, made of polyimide (PI, elastic modulus 2.5 GPa), 11.9 µm-thick Cu (elastic modulus 119 GPa) and 25.4 µm-thick adhesive (elastic modulus 931 MPa), had the cross section from top to bottom of 25.4 µm PI/Cu/12.7 µm PI/adhesive/Cu/25.4 µm PI/Cu/adhesive/12.7 µm PI/Cu/38.1 µm PI. Together with the core/shell package, the flexible circuits were mounted on a phantom skin (elastic modulus 130 kPa).

Results and Discussion

Soft, Wireless, Skin-Integrated Platform for Intraoperative Monitoring

Figure 1A:
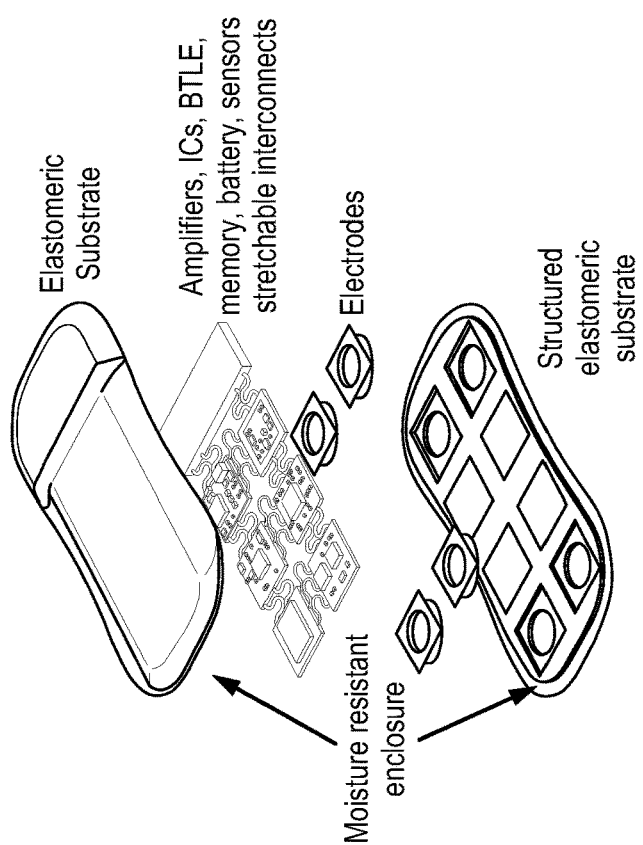
Figure 1C:
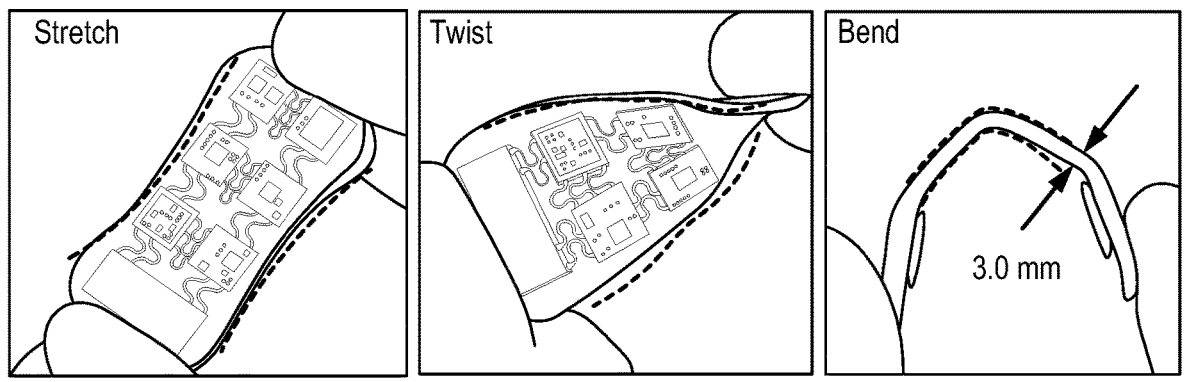

Recent advances in materials, mechanics designs and manufacturing methods establish the foundations for classes of thin, mechanically compliant electronic systems that enable multimodal sensing on the surface of the skin at nearly any body location. As demonstrated herein, these platforms combine high performance electronics and biosensors with wireless functionality to achieve high accuracy monitoring of muscle activity in response to nerve impulses and intraoperative stimulation. FIG. 1A presents a schematic, exploded view of the design. The functional subcomponents distribute across a collection of 'islands' that interconnect electrically and mechanically via narrow, filamentary serpentine traces, optimally configured to create low modulus, 'spring-like' mechanics in geometries guided by computational modeling of the mechanical and electrical characteristics. Encapsulating this 'island-bridge' mesh network above and below with a low modulus, silicone elastomer defines skin-compatible physical properties, as a soft and comfortable interface to the skin (FIG. 1B). The resulting form factor and intimate skin interface are strikingly different than those of conventional wearable devices, in which rigid packaged electronic components mechanically attach to the skin via straps, penetrating pins, tapes, or bands. Stretching, twisting, bending and other complex modes of deformation can be accommodated without altering functional operation (FIG. 10). Robust, comfortable coupling to the skin even at tightly curved regions of the anatomy (e.g.

ankle) and sensitive parts of the body (e.g. face) are possible, thereby supporting dual s-EMG and motion sensing from multiple high-flexion or contractile muscle groups, in a mode that is mechanically imperceptible to the patient and physically confined without restricting the physician.

Figure 5A:
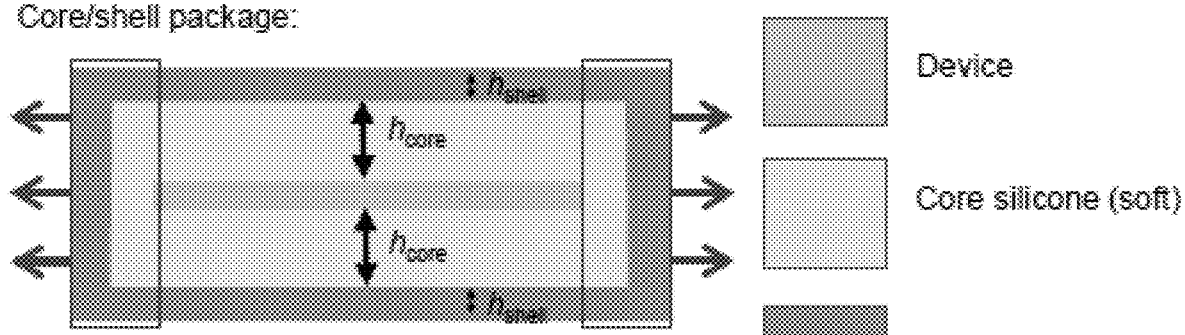
FIGS. 5A-5C. Mechanics simulations for the effective modulus of the conformable device with FIG. 5A core/shell FIG. 5B standard designs.
Figure 5B:
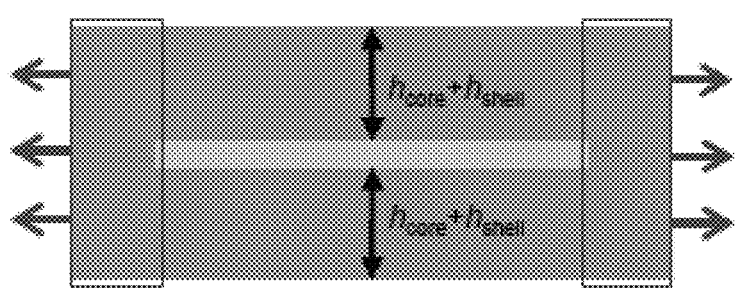
Figure 5C:
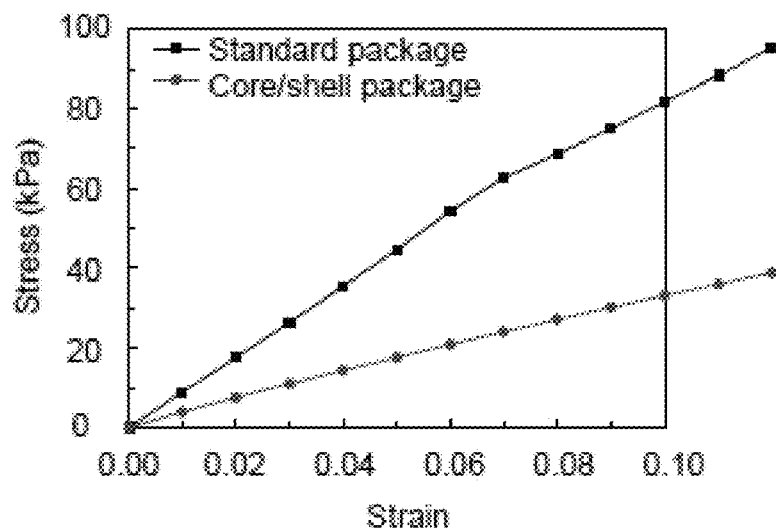

An enhancement of the conformable device designs used here involves embedding the active components in an ultra-low modulus silicone formulation (3-5 kPa) as a core, with a surrounding thin silicone shell that has a slightly higher modulus (50-100 kPa). This core/shell configuration allows additional degrees of freedom and motion of the serpentine interconnect structures, thereby leading to an effective modulus of 390 kPa, much smaller than that of standard designs (890 kPa) (FIG. 5). The average thickness (~2.5 mm), the physical size (3.4×6.6×0.3 cm$^3$) and the weight (7 g) of such devices are similar to those of a standard gauze patch, qualitatively differentiated from any alternative commercial monitoring system currently available.

The functional electrical components include a Bluetooth® Low Energy Smart radio, flash memory module (32 MB), 3-axis accelerometer and gyroscope, an analog-front end that connects to two Ag/AgCl electrodes (single lead configuration), and a rechargeable battery (15 mAh; 10×25×1.6 mm$^3$; wirelessly charging) that enables simultaneous measurement of motion and s-EMG signals for up to ~16 h. The accelerometer has an adjustable sampling rate (12-50 Hz), 2-mg sensitivity, and 12-bit resolution, sufficient to capture fine muscle movements, twitching, and spasms. The analog front-end samples s-EMG signals at 250 Hz with an amplification factor of 21.6 dB and a band-pass filter from 0.5-125 Hz. The low-end corner filtering is a byproduct of the AC-coupled relationship between the Ag/AgCl electrodes and amplifier electronics, while the high-end is set by the analog front-end to satisfy the Nyquist condition of the analog-to-digital converter (ADC).

Quantitative Analysis of the Mechanical Attributes

Figure 1D:
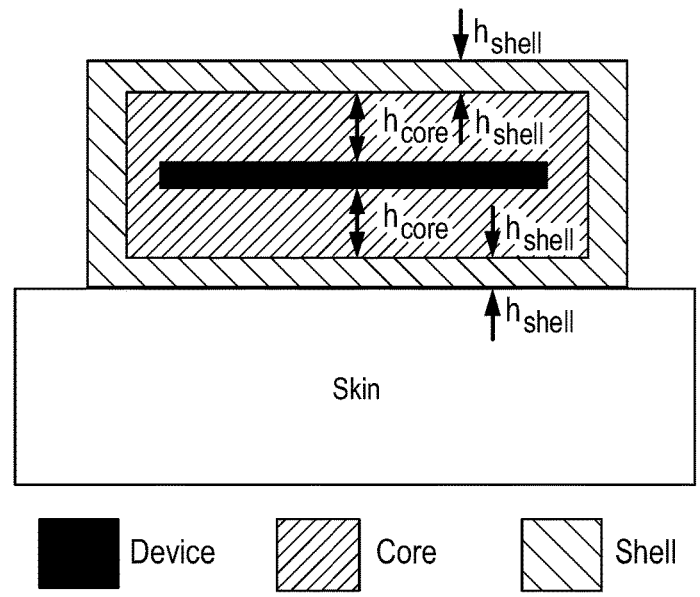
Figure 1E:
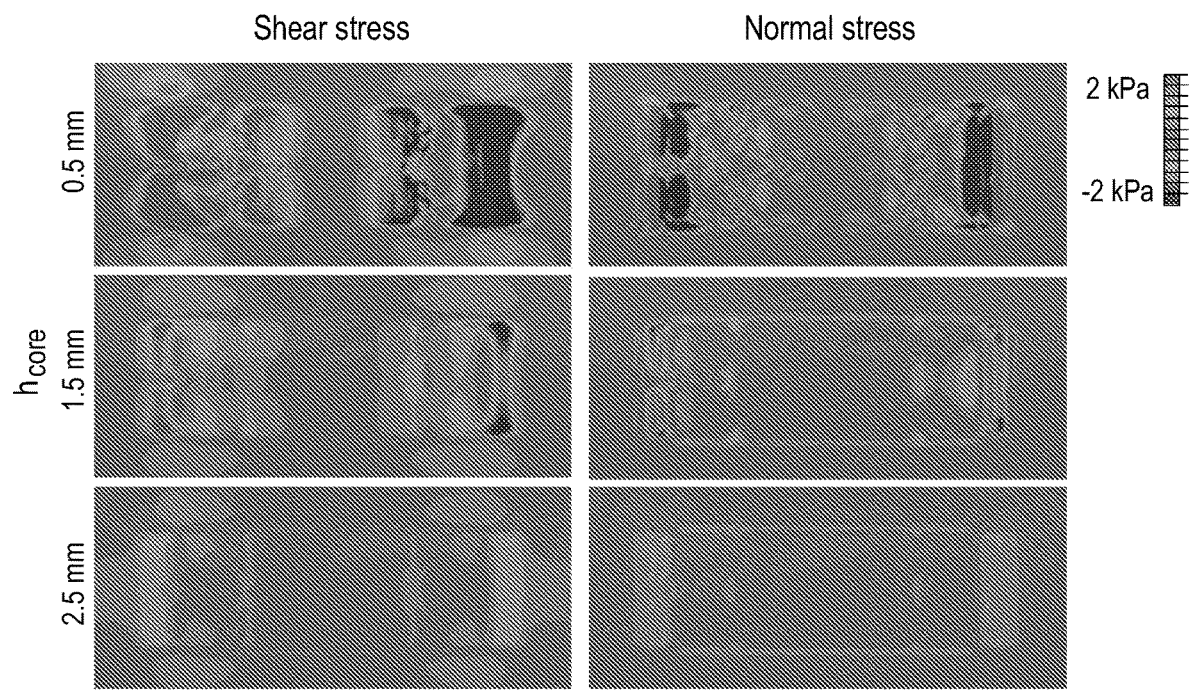
Figure 1F:
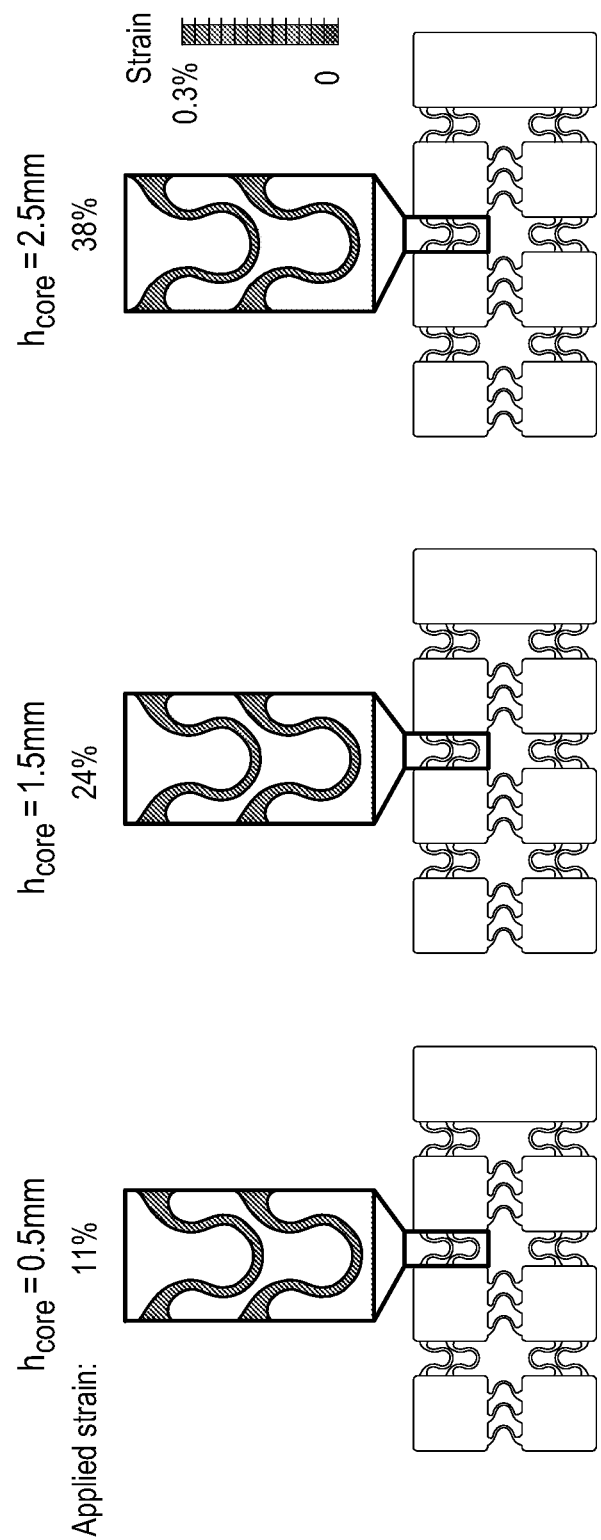
Figure 6A:
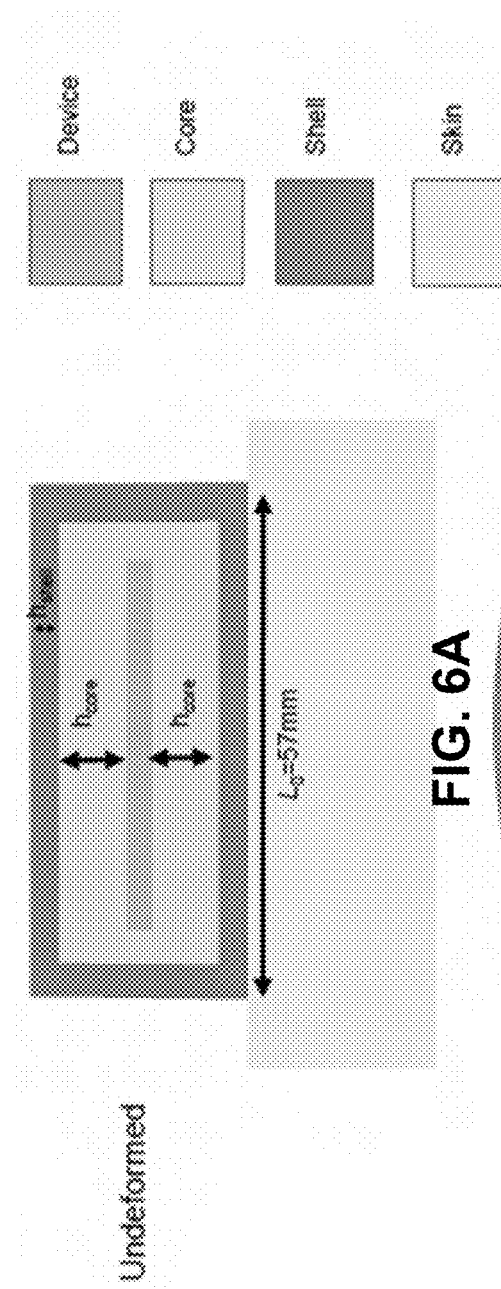
FIGS. 6A-6B. Bending simulation of material layers and geometrical parameters for an example conformable device.
Figure 6B:
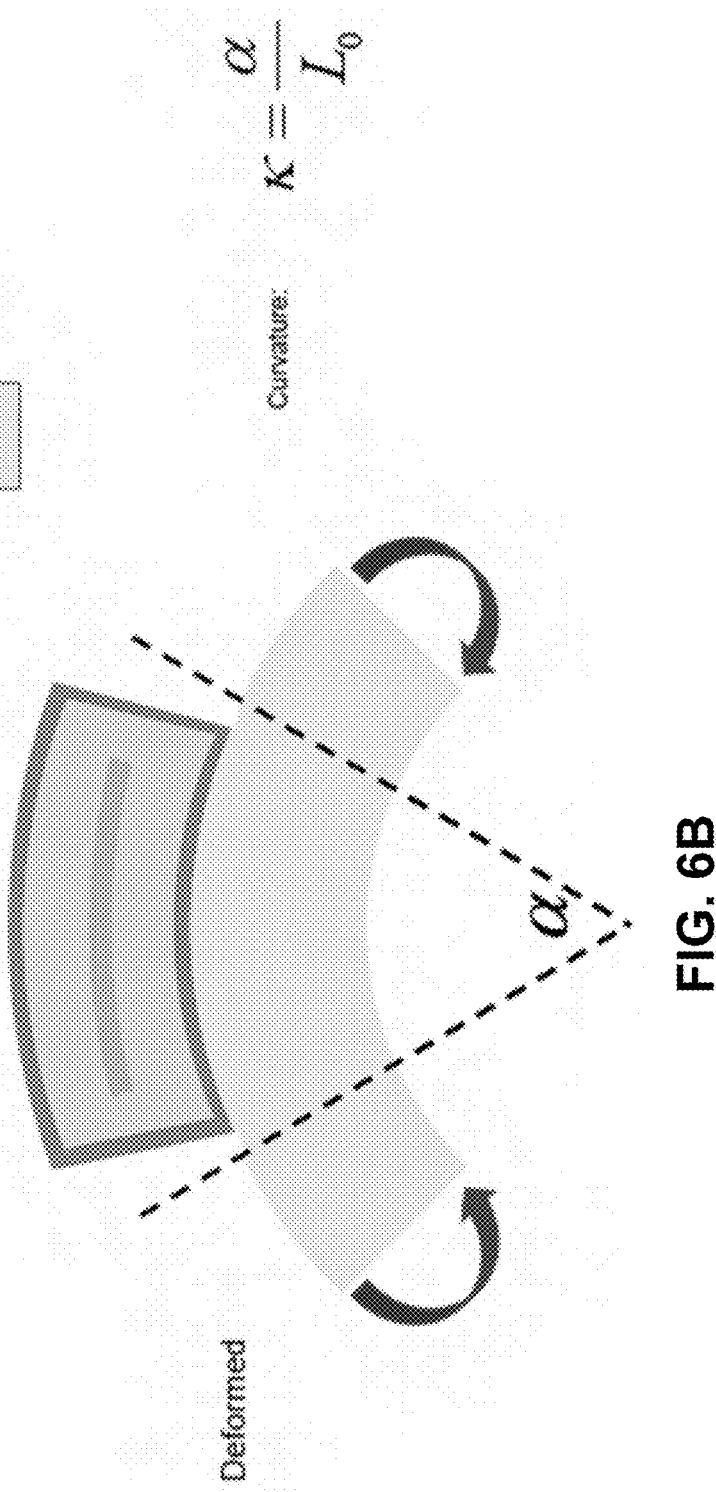
Figure 7:
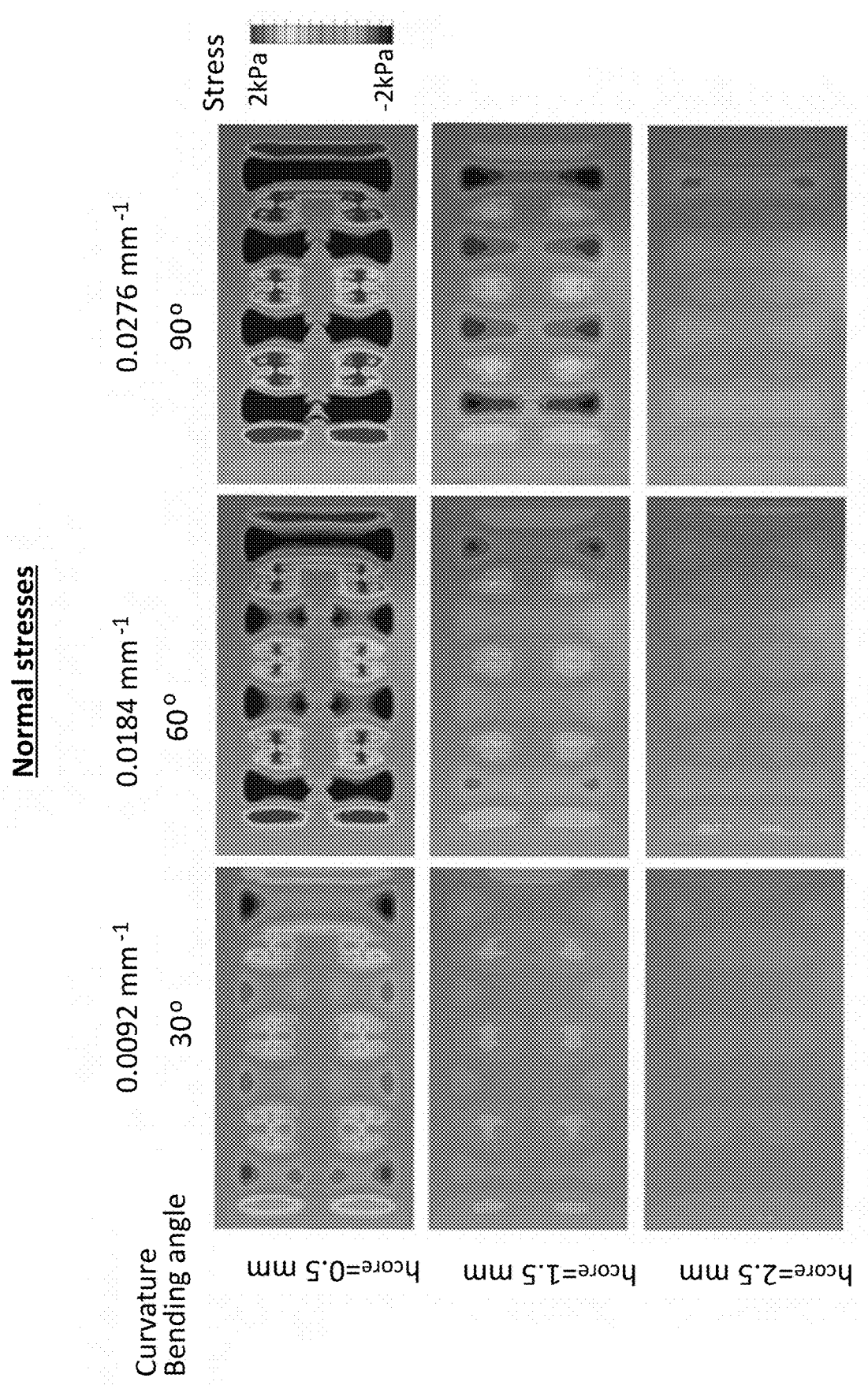
FIG. 7. Spatial distribution of stress induced at the interface with skin in response to varying curvatures and bending angles. The normal stresses vary with core thicknesses at 0.5 mm, 1.5 mm and 2.5 mm.
Figure 8:
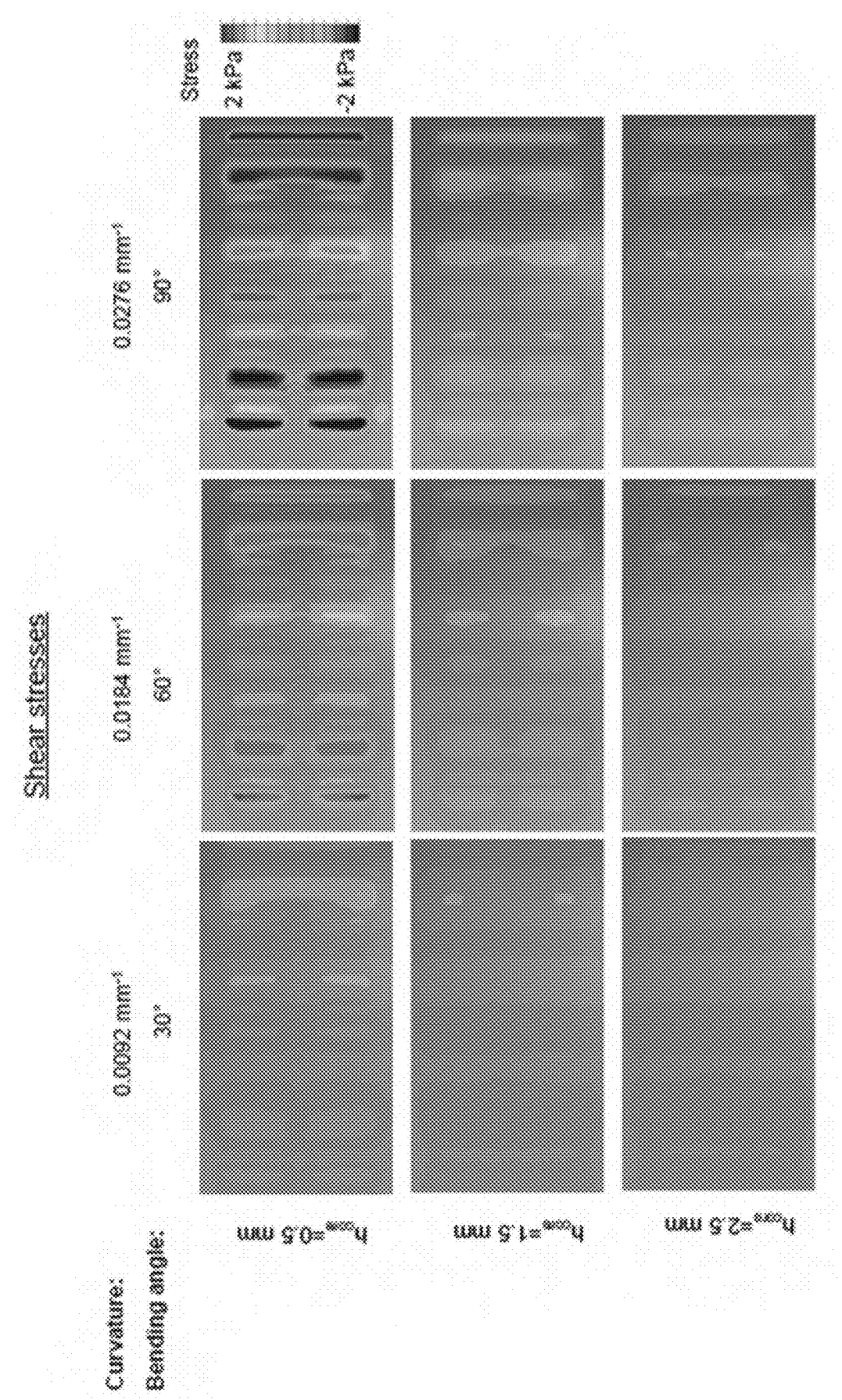
FIG. 8. Spatial distribution of stress induced at the interface with skin in response to varying curvature and bending angle. The shear stresses vary with core thicknesses at 0.5 mm, 1.5 mm and 2.5 mm.
Figure 9:
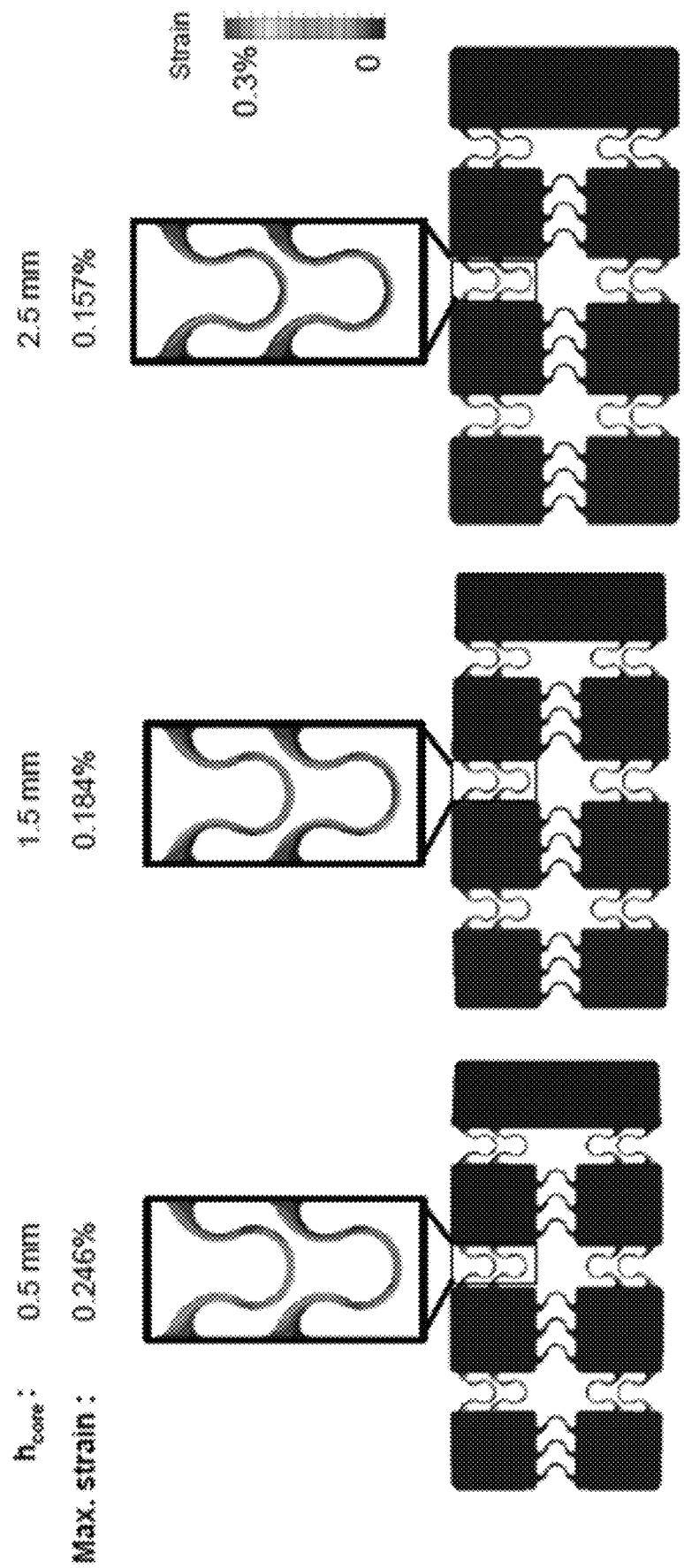
FIG. 9. Spatial distribution of strain in the circuit elements in response to a fixed curvature and bending angle for different $h_{core}$ and the maximum strain that results.

FIG. 1D presents a schematic cross-sectional illustration of the design (as in FIGS. 1A and 1B) in the core/shell configuration described above. The shell provides mechanical stability, elastic restoring force and skin-compatible interface; the core allows the island/bridge construct to mechanically deform freely, thereby minimizing the material strains induced by system deformation. Additionally, optimized choices for the thickness of the core (Silbione, elastic modulus 3 kPa, and thickness, $h_{core}$ in FIG. 1D), guided by computational mechanics, suppress stresses that can result from mechanical loading of the surface of the skin. Simulation results summarize the dependence on $h_{core}$ for the case of 20% tensile strain at the system level (FIG. 1E, FIG. 5). The interfacial stresses for $h_{core}$=0.5 mm and 1.5 mm lie below values associated with thresholds for sensation in the underlying skin (~2 kPa) in most regions; $h_{core}$=2.5 mm enables even further reductions. FIG. 1F shows the strain distributions in the first copper interconnect layer from the top, for the case of an applied strain that corresponds to the limit of elastic stretchability (with yield strain of ~0.3% in copper). In all cases, the strains in the island regions are negligible. The stretchability increases with $h_{core}$ (FIG. 1F) to levels comparable or larger than the elastic limit of human skin. The results in FIGS. 1 (E and F) highlight the advantages of large values of $h_{core}$ (~2.5 mm). Computed results for bending appear in FIGS. 6-9. FIGS. 7 and 8 show the distributions of interfacial stresses on the skin for different curvatures ($\kappa$=0.0092 mm$^{-1}$, 0.0184 mm$^{-1}$ and 0.0276 mm$^{-1}$), corresponding to different bending angles ($\alpha$=30°, 60° and 90°) as shown in FIG. 6. Even at large flexion angles)(~90°, the interfacial stresses for $h_{core}$=2.5 mm are below threshold values for skin sensation (~2 kPa). The corresponding strain distributions in the copper fall within the elastic limit for all three cases (i.e. $h_{core}$=0.5 mm, 1.5 mm and 2.5 mm).

Quantitative Comparisons of Usability and Signal Fidelity to Clinical Standards

Current state-of-the-art intraoperative monitoring systems provide high quality signal recordings, but they are large and complex, and the costs of the equipment and of the trained personnel necessary for its operation are prohibitive. Additionally, the wired connections and computer consoles needed to analyze and display data (FIG. 10) are cumbersome for surgeons and support staff in the operating room. A conventional system of this type (Cascade® IONM) offers high sampling rates (25.6 kHz), high signal resolution (18-bit) and low noise operation (<2 $\mu V_{RMS}$) optimized for EMG recordings, with penetrating needle electrodes or surface electrodes as the measurement interface. By contrast, the conformable device embeds all necessary electronics and electrodes in a single, compact platform that, itself, softly couples to the skin in a straightforward, non-invasive manner, without need for specialized skill or training, to nearly any region of the body. Although the conformable device may not be hermetically sealed, the silicone encapsulation layer prevents water ingress, and thereby mitigates risks of moisture exposure to the circuitry during intraoperative monitoring procedures. The overall size (~2 orders of magnitude) and mass (~2 orders of magnitude) of the conformable device are qualitatively smaller than those of conventional hardware used for intraoperative monitoring. The wireless, battery-powered operation and intimate skin interface isolates the system from noise associated with power lines, motion artifacts and ambient electrical interference, as demonstrated in our previous systems. Although sampling frequencies and levels of resolution (100 $\mu V_{RMS}$, 1 kHz and 16-bits) are somewhat lower than those of conventional systems, the quality of the data determined by signal-to-noise ratio (SNR) analysis in practical clinical contexts, is comparable (to within ~1 dB) to that of s-EMG research tools (Delsys EMG recording system, FIG. 11). Further improvements in SNR can achieved by employing thin hydrogel layers between the skin and the recording electrodes.

Monitoring of Nerve-Muscle Function During Surgeries on the Peripheral, Spine, and Cranial Nerves Standard neurosurgery procedures expose targeted nerves identified for tumor removal, decompression, grafting, or other medical purposes (see methods for more details). In this context, direct nerve electrical stimulation represents a common neurosurgical technique for locating, visualizing, and assessing the health of neural-muscle interfaces. Here, electrical current pulses excite nerves and polarize neuronal cell membranes, thereby producing an action potential in the nerves that leads to muscle contraction (23, 24). The induced activation of the muscles generates a corresponding EMG response, typically recorded with penetrating needle electrodes and large-scale data acquisition systems. The minimum current that elicits a measurable EMG signal defines the stimulation current threshold. This response is strongly non-linear, with zero signal below this threshold and a smooth, monotonic increase with current above it, until saturation at some upper limiting value. With the known distance between the stimulation and measurement sites, these data allow determination of the nerve conduction velocity, a metric that highlights and characterizes nerve damage. Although threshold levels vary according to different physiological factors and the relative location of the nerves and muscle groups, comparison of measured thresholds serves as an effective means to compare the performance of the skin-interfaced conformable devices reported here with clinically established tools. This approach simply quantifies the comparisons; clinical use typically involves stimulation at levels significantly above threshold.

The clinical studies involved conformable devices placed on one or more muscles innervated by the target nerve with consenting patients undergoing needle EMG recordings using a state-of-the-art intraoperative monitoring system during peripheral nerve, spine, or cranial nerve surgical procedures (at Northwestern Memorial Hospital). We compared measurements from the conformable device platform to those using two types of EMG electrodes with hard-wired interfaces to conventional data acquisition and conditioning electronics: needle electrodes (with Cascade® IONM electronics) and surface electrodes (also with Cascade® IONM electronics) (Table S1). All three types of recording systems (Tables 1-3) were applied (FIG. 2A) near the surgical access point to the common peroneal nerve (FIG. 2B) for capture of EMG during stimulation.

TABLE 1

Summary of Peripheral Surgery Patient Information

| Patient | Stimulated Nerve | Recorded Muscle | Age | Gender | Surgery |
| --- | --- | --- | --- | --- | --- |
| 1 | Right tibial nerve | Right tibialis anterior muscle | 52 | F | Decompression of a severe sciatic nerve stretch injury involving primarily the peroneal portion |
| 2 | Distal tibial nerve | Sole of foot muscle | 19 | F | Neurofibroma dissection |
| 3 | Right spinal accessory nerve | Right trapezius muscle | 37 | M | Neurotization with severe right brachial plexus injury |
| 4 | Right common peroneal nerve | Right peroneuslongus muscle | 24 | M | Decompression and neurolysis with severe right common peroneal nerve injury |
| 5 | Right tibial nerve | Right sole of foot muscle | 60 | M | Neurotization With laceration injury to peroneal portion of sciatic nerve in thigh |
| 6 | Right tibial nerve | Right sole of foot muscle | 47 | F | Schwannoma removal from right tibial nerve in the calf |
| 7 | Right C6 spinal nerve | Deltoid muscle | 41 | F | Schwannoma removalfrom the middle trunk of her right brachial plexus |
| 8 | Left Common peroneal nerve | Left tibialis anterior muscle | 48 | M | Decompression of left common peroneal nerve with prior surgeries for treatment of a ganglion cysts |
| 9 | Right common peroneal nerve | Right tibialisanterior muscle | 54 | M | Decompression of right common peroneal nerve with a ganglion cyst |
| 10 | Left posterior interosseous nerve | Finger extensor digitorum muscle | 45 | M | Schwannoma removal from left posterior interosseous nerve |

TABLE 2

Summary of Spinal Surgery Patient Information

| Patient | Stimulated Nerve | Recorded Muscle | Age | Gender | Surgery |
| --- | --- | --- | --- | --- | --- |
| 1 | Scarred right L5 spinal nerve | Tibialis anterior muscle | 30 | M | Right L5/S1 spinal surgeries |
| 2 | Left L5 spinal nerve | Tibialis anterior muscle | 60 | F | Corrective surgery for scoliosis |
| 3 | Left L5 spinal nerve | Tibialis anterior muscle | 69 | F | Lumbar decompression and fusion spine surgery |
| 4 | Scarred leftL5 spinal nerve | Tibialis anterior muscle | 57 | M | L4/5 surgeries |

TABLE 3

Summary of Cranial Surgery Patient Information

| Patient | Stimulated Nerve | Recorded Muscle | Age | Gender | Surgery |
| --- | --- | --- | --- | --- | --- |
| 1 | $7^{th}$ Cranial Nerve (facial) | Left Facial Muscle | 43 | M | Removal of left cerebellopontine angle epidermoid mass |

TABLE S1

Comparison between Cadwell Cascade and Conformable Device Data Acquisition System, as described herein

| System parameters | Cadwell Cascade | Conformable Device |
|---|---|---|
| Sampling Rate | 25.6 kHz | Up to 1 kHz |
| Gain | 2-1000 | 2-12 |
| Resolution | 18 bits A/D | 16 bits A/D |
| Bandwidth | Up to 12.8 kHz* | Up to 500 Hz |
| Range | From 0.01 μV | 6 μV-400 mV$_{PPK}$ |
| Analog Filter | 2-pole high-pass, low-pass filter (12 dB/octave), and 60 Hz notch filter | High-pass filter at 0.5 Hz; Low pass filter at Nyquist Frequency (e.g. 125 Hz @ $f_{SAMPLE}$ = 250 Hz) |
| Noise | <2 μV$_{RMS}$ | <100 μV$_{RMS}$ up to $f_{SAMPLE}$ = 1 kHz |

*Bandwidth of Needle-EMG based on Nyquist rate

As outlined herein, such measurements revealed that stimulation current thresholds determined using the conformable device were statistically indistinguishable from those determined using Cascade® electronics coupled to needle electrodes and surface electrodes (FIG. 2C). In addition to high quality electrical measurements, the conformable device supports motion sensing with an integrated accelerometer, as a complementary data stream for detecting muscle activation, where mechanical response serves as the basis of measured signal. In FIG. 2D (top 3 traces), motion recorded using a tri-axis accelerometer captures small mechanical vibrations caused by contractions of the tibialis anterior muscle group. The mechanical activation profiles observed in the y- and z-planes align with the induced EMG response of the subjacent muscle group (FIG. 2D, bottom trace). Multimodal sensing in this manner enables tracking of both electrical and mechanical signatures of muscle activity, to provide redundancy in monitoring of muscle response and to enable compensation for motion induced artifacts. This capability could also provide insight into the depth of anesthesia (29-31). In control experiments, we tested for the presence of motion or other artifacts by positioning the nerve stimulator probe above threshold at a neighboring non-neural tissue site, and showed that stimulation of non-neural tissue does not generate measurable EMG signals (FIG. 12). Although motion detection represents an area of opportunity, the work reported here focuses on EMG because of its use as the current standard of care.

Figure 3A:
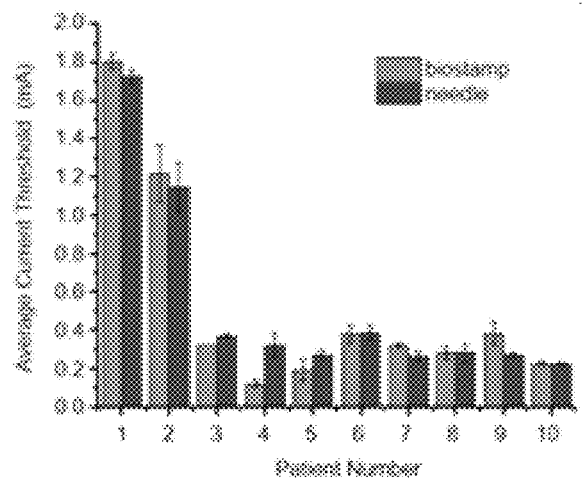
Figure 3B:
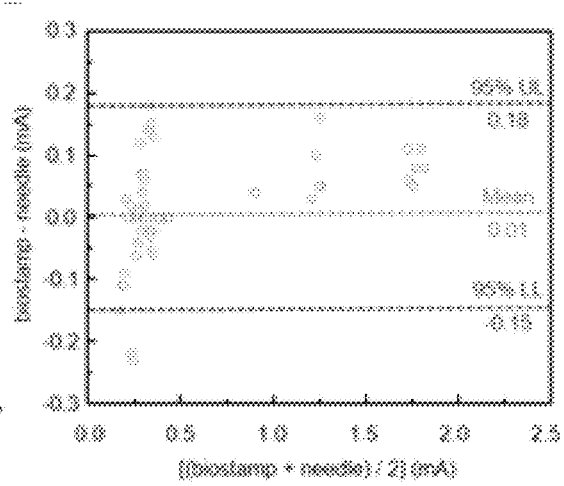
Figure 3C:
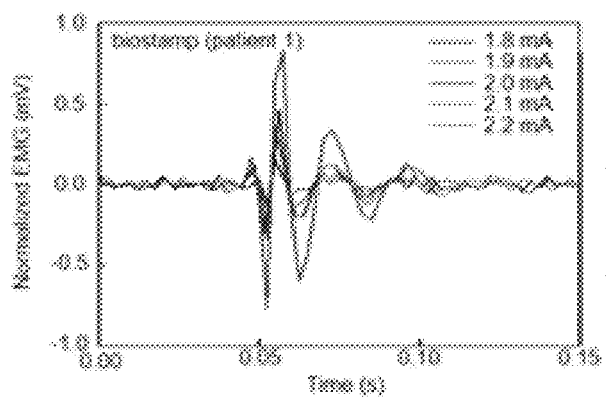
Figure 3F:
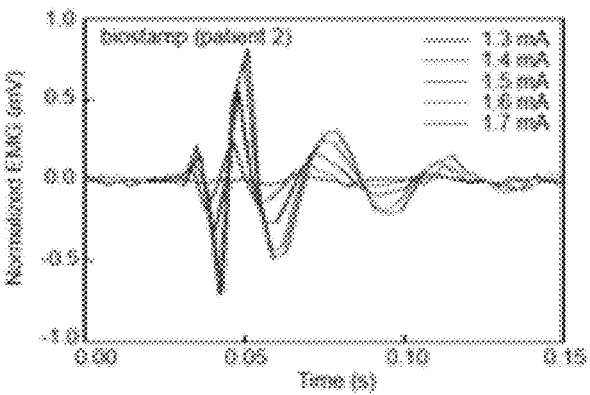

In careful comparative studies in patients undergoing peripheral nerve surgery, conformable devices detected average current thresholds similar to those reported for conventional monitoring systems with needle electrodes (FIG. 3A; n=10 patients). The precise placement of the conformable device is less susceptible to noise as the conformable device can detect average threshold currents similar to the conventional needle-based monitoring system. The conformable device and the needle-based system strongly correlated with nearly 95% of the two data sets falling within +0.18 mA and −0.15 mA (FIG. 3B), across n=55 peripheral nerve surgery subjects.

This finding is important, partly because the morphology of the s-EMG waveforms captured by the conformable device had lower peak amplitudes and different decay envelopes compared to those recorded with needle electrodes in the conventional manner. The differences in amplitude varied across subjects, likely influenced by the position of the surface electrodes and the nature of the skin barrier in the case of the conformable device, and the precise placement of the needle electrodes in the case of the clinical standard. The data envelopes depend on the sampling rates and the frequency dependent electrical impedance, both of which are different for these two systems.

Examination of representative data (patients 1 and 2) highlight some of the key findings. For patient 1, the conformable device and conventional needle platforms both exhibited current thresholds in the ~1.8-2.2 mA range, and high quality signals with stimulation levels commonly applied during neurosurgery (FIGS. 3, C and D). Specifically, the EMG waveforms captured by the conformable device exhibit SNR values of ~10 dB at threshold and reach ~50 dB in response currents employed during routine neurosurgery procedures (FIG. 3E). The needle electrode system offers improved SNR, but in clinical terms, SNR thresholds above 10 dB are equivalent, in the sense that they offer routine ability for threshold detection. For patient 2, the EMG waveforms also showed robust muscle signal patterns in response to current stimulus levels in a safe operating range (FIGS. 3, F and G). Similar to the measurements in patient 1, the SNR levels for the needle electrode platform (~60 dB) and conformable device (~30 dB) were well above the noise at the threshold current level (conformable device: 1.4 mA, needle: 1.3 mA), and increased with current in an expected manner above threshold (1.3-1.7 mA, FIG. 3H). The differences in signal levels between these two systems largely depend on the electrode placement and stimulation location. Increasing the stimulus current resulted in increasingly large muscle responses, up to EMG amplitudes of ~0.15 mV for the conformable device and ~0.4 mV for the needle electrode platform. In both cases, the SNR was sufficiently high to detect muscle activation, throughout the normal range observed during surgical procedures.

Figure 4A:
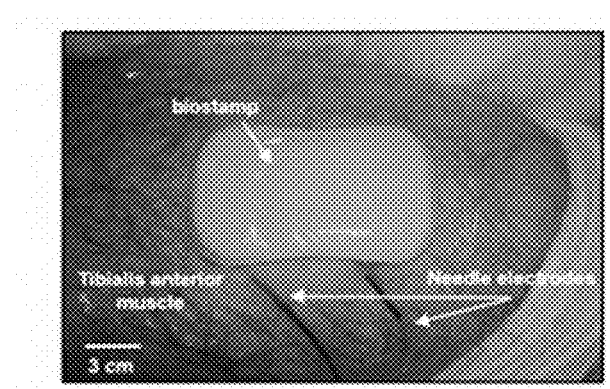
FIGS. 4A-4F. Comparison of the quality of EMG signals captured using the conformable device and conventional equipment (needle electrodes and standard recording electronics) during spinal and cranial nerve surgeries.
Figure 4D:
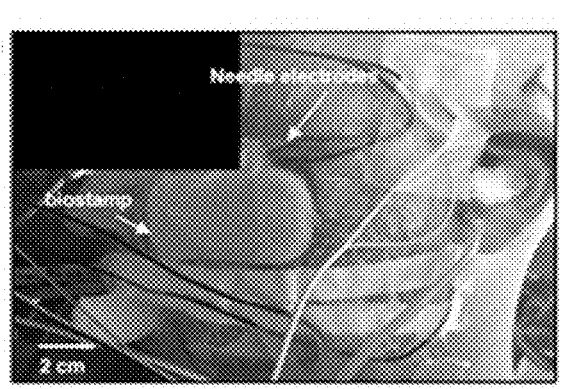
Figure 4B:
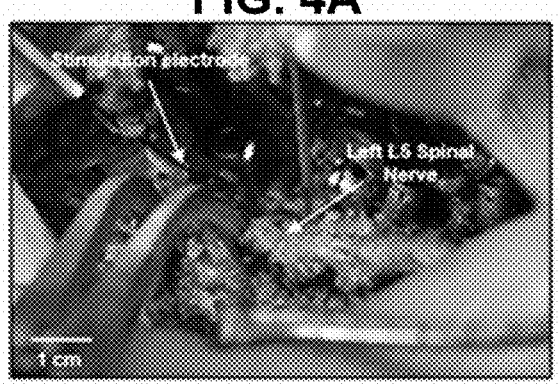
Figure 4E:
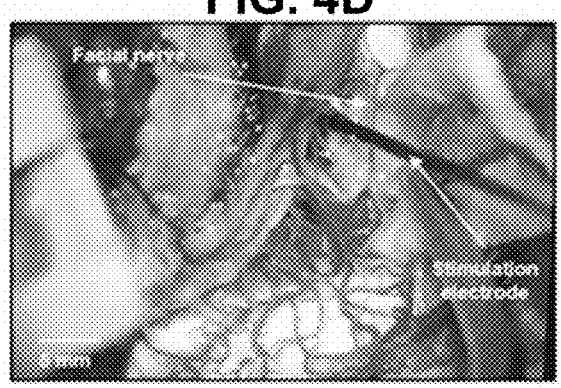
Figure 4C:
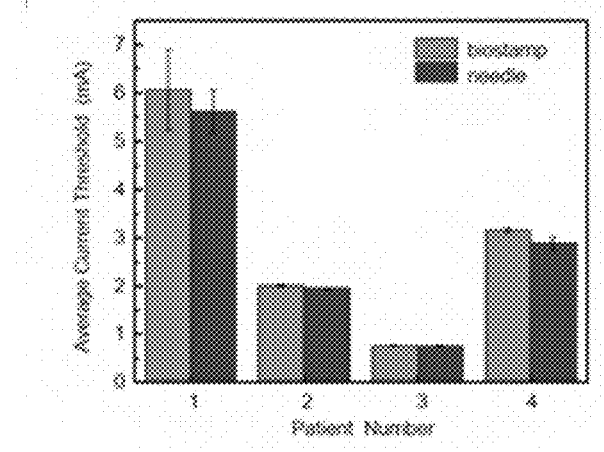
Figure 4F:
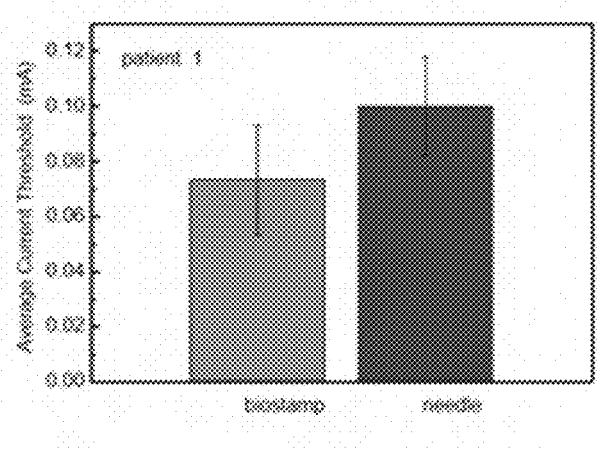
Figure 13A:
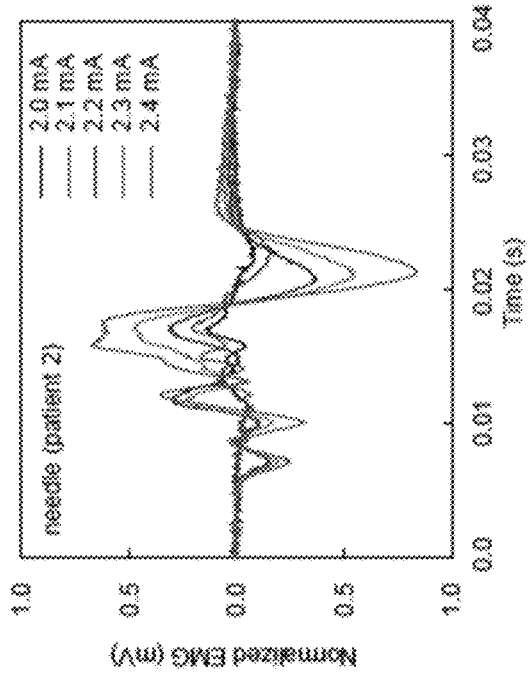
FIGS. 13A-13C. Example conformable device s-EMG signals as function of direct nerve stimulation current during spinal surgery (patient 2 from FIG. 4C).
Figure 13B:
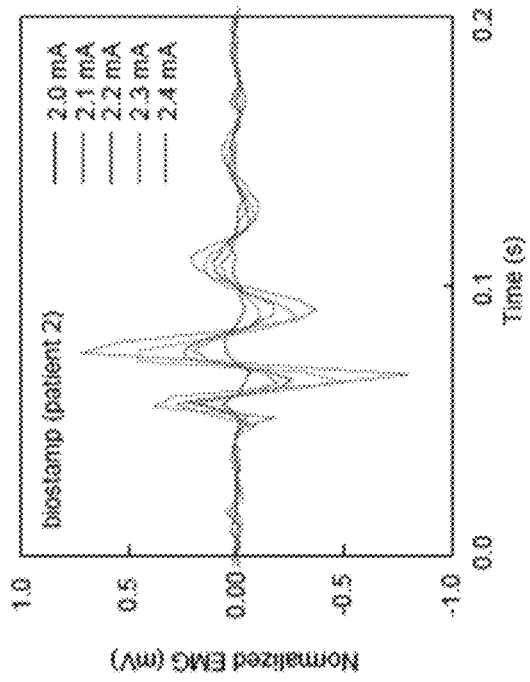
Figure 13C:
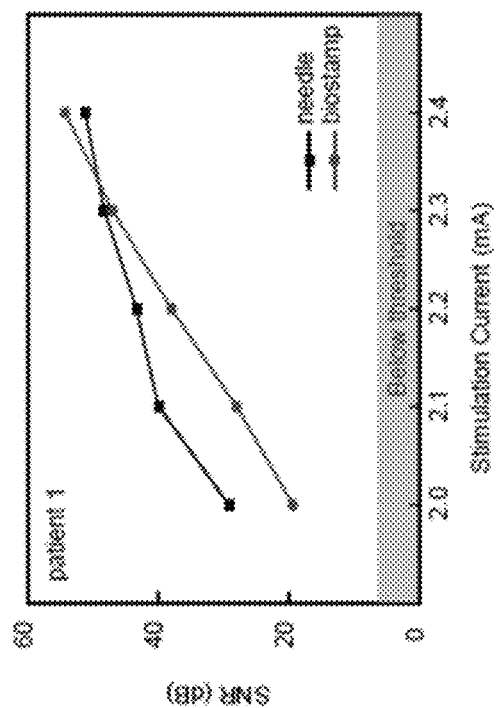

In addition to peripheral nerve surgeries, the conformable device can provide intraoperative monitoring insights during spinal and facial nerve stimulation. As in the other cases, in spinal nerve procedures, current threshold levels for the conformable device were consistent with those of needle electrode platform (FIG. 4, A-C). Across all four patients examined, threshold values determined by the two platforms are comparable, ranging from ~1-7 mA (FIG. 4C). As before, EMG waveforms measured by the conformable device and the needle electrode platform had SNRs well above the noise floor (>10 dB). In both cases, the SNR increases with stimulation current level but approached similar values above 2.3 mA (FIG. 13), indicating that the nerve fibers are activated, and thereby causing a saturated muscle response. In facial nerve procedures, the measured current thresholds using the conformable device and needle electrodes were also similar (FIG. 4, D-F). Taken together, these findings demonstrate the broad applicability of the conformable device for intraoperative monitoring across multiple, highly sensitive nerve targets.

DISCUSSION

The results presented here demonstrate that wireless, skin-mounted device technologies that exploit soft mechanics, multifunctional electronics and precision biosensors enable continuous electrical and mechanical monitoring of muscle responses during peripheral nerve, spine and cranial surgeries. The ultra-soft, miniaturized form factor facilitates direct attachment to a broad range of muscle groups, including challenging regions of the anatomy such as the face. The result is a non-invasive, easy-to-use platform for capturing EMG and motion signals, with capabilities that reproduce the key functionalities of conventional, large-scale electronic platforms, which serve as the current clinical standard of care (FIGS. 3 and 4, and FIG. 6).

Figures 19A, 19B, 19C:
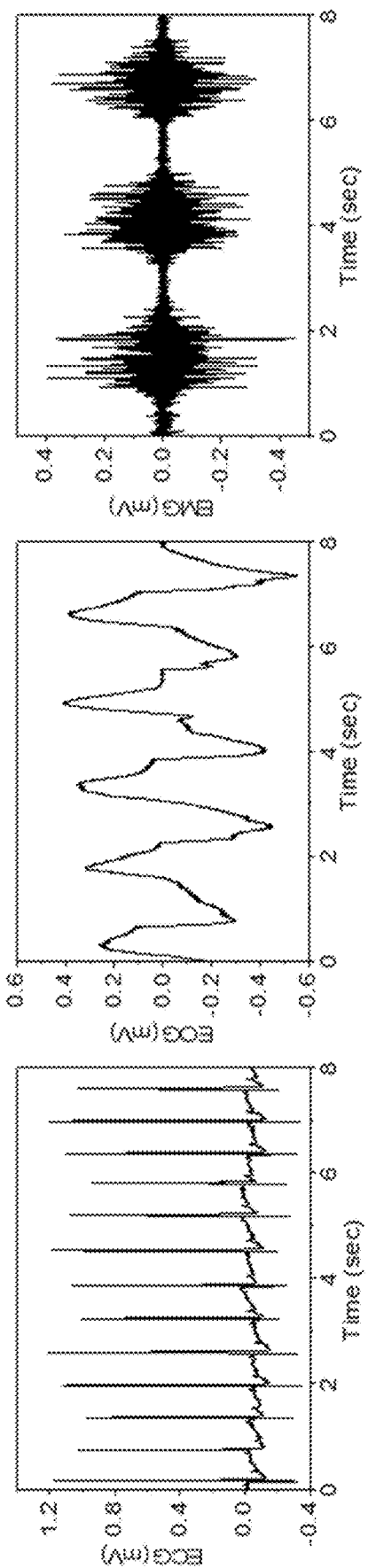
FIGS. 19A-19C illustrate simultaneous operation of multiple conformable devices, which measure electrocardiogram (placed on chest) (FIG. 19A), electrooculogram (placed on side of forehead) (FIG. 19B) and electromyogram (placed on bicep) (FIG. 19C).

Compared to the established intraoperative monitoring systems (Cadwell® Cascade® IONM), the physical design of the conformable device offers significant advantages in multimodal sensing (electrophysiology and accelerometry), size, weight, and comfort, without any practically significant sacrifices in signal fidelity or threshold detectability for intraoperative monitoring. The simplicity of operation eliminates the need for personnel with specialized training in needle electrodes and EMG recording. These usability attributes, taken together with the wireless mode of operation, offer the potential to significantly simplify clinical preparation effort and time in the operating room. In particular, the heavy demands associated with needle electrodes, the complex procedures for insertion into the tissue, and the management of wired cables that must be secured to the body of the patient and routed across the operating room table to adaptor boxes and computer control systems could be greatly minimized. FIG. 14 provides a series of EMG recordings obtained from the flexor carpi radialis muscle of a human subject to confirm recording stability of the conformable device over the duration of a typical surgery (<10 hours). The EMG amplitude and SNRs stimulated by maximum voluntary muscle contraction in recordings remain the same (±0.2 V and 2.8 dB) during 10 hours of wearing, which ensures the recording stability throughout the duration of a surgery. In addition, conformable devices are placed in multiple body locations to measure electrical potentials simultaneously. Concurrent monitoring of EMG, electrocardiography (ECG) and electrooculography (EOG) offers complimentary diagnostic capabilities during neurosurgical procedures (FIG. 19).

These attractive physical and operational characteristics can serve to drive procedural uptake in hospitals where complex and expensive monitoring equipment is unavailable or untenable. The ease of setup offers significant benefit to medical facilities with untrained personnel, thereby significantly broadening access to intraoperative monitoring. In addition, the soft form factor and ability for attachment to multiple body locations make this type of technology applicable across a variety of surgical procedures and clinical scenarios. For example, these platforms could be used to monitor unintended stretching of the sciatic nerve during hip surgery and the axillary nerve during shoulder surgery, both of which represent common complications of orthopedic procedures. Real-time monitoring of salient nerve health to minimize intraoperative nerve damage during parotidectomies represents another intriguing possibility. Other types of demanding surgeries where peripheral nerves are vulnerable, and where monitoring could be valuable, include procedures targeting the neck, where the spinal accessory nerve is susceptible to damage, as well as the abdomen and pelvis, where the lumbosacral plexus is at risk. The ease of use suggests the possibility for many other clinical applications of these technologies in monitoring nerve muscle integrity.

More generally, the successful application of conformable device in a surgical context foreshadows other modes of operation in different clinical use cases. Specifically, many recently reported 'soft' sensor technologies can easily be incorporated into the conformable device platform to capture additional physiological parameters of interest. Examples include blood flow, blood pressure, temperature, hydration state, tissue stiffness, mechano-acoustic signatures, swelling and many others. Electrical and thermal stimulation represent additional actuation possibilities. These unique sensing and actuation capabilities could enable monitoring over a broad range of surgeries beyond neurophysiological procedures. For example, in reconstructive surgical procedures, the state of health of various types of tissue flaps could be monitored by measuring blood flow in the region of the transplanted tissue and from the feeding arteries. To surveil and prevent skin pressure ulcers in immobile patients, diabetics and those with peripheral neuropathies, these added sensors and actuators could be applied to measure tissue stiffness, hydration, swelling, and temperature, providing early warning signs of tissue breakdown and ulcers. The onboard processor and wireless connectivity in combination with the conformable device sensors and actuators would ultimately allow operation in an automated mode as part of a closed loop system, which senses for skin and muscle injuries, and in turn, delivers therapy (via drug release, thermal activation or electrical stimulation).

In summary, soft mechanics, compact size and wireless modes of operation in advanced skin-mounted electronic sensing technologies have the potential to fundamentally improve the state of intraoperative monitoring during neurosurgical procedures. Based on our clinical studies, the combination of conformable device measurement platforms and traditional stand-alone nerve stimulators can provide surgeons with the opportunity to monitor nerve and muscle function during a wide range of operations in which nerves are at risk of damage. Adoption of this class of wireless wearable technology may not only simplify the state of intraoperative monitoring, but also improve patient outcomes during invasive surgical procedures.

Figure 15:
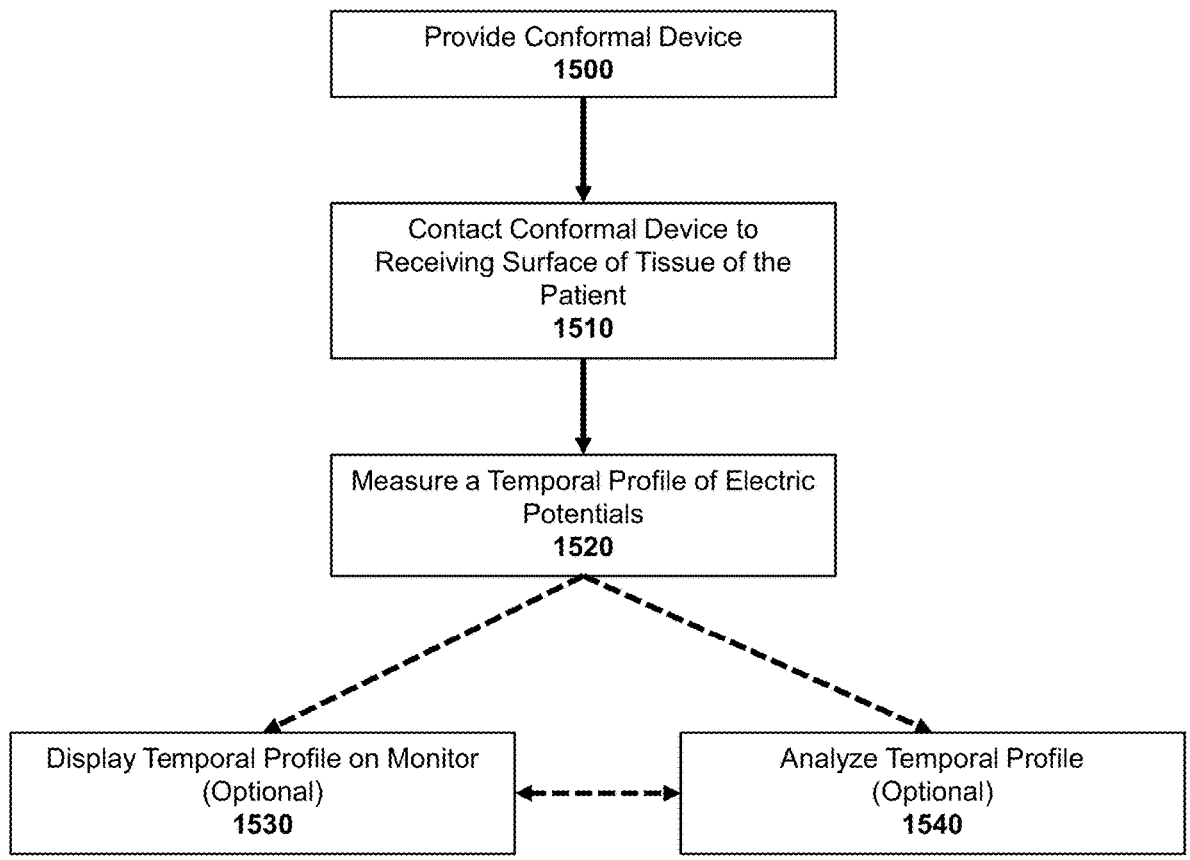
FIG. 15 provides a flow chart of an exemplary method described herein.

FIG. 15 provides a flow chart of an exemplary method described herein. First, a conformal device as described herein is provided 1500. Then the conformal device is place in conformal contact with a tissue receiving surface, for example, the skin of a patient 1510. Then the conformal device measures a temporal profile of electric potentials, which may be expressed in various forms including electromyographic waves 1520. In some cases, it may be beneficial to display the temporal profile, for example, during a surgical procedure so that the surgeon may monitor nerve activity 1530. Optionally, the temporal profile may be analyzed, for example, by a processor which may be included in the monitor 1540.

Figure 16:
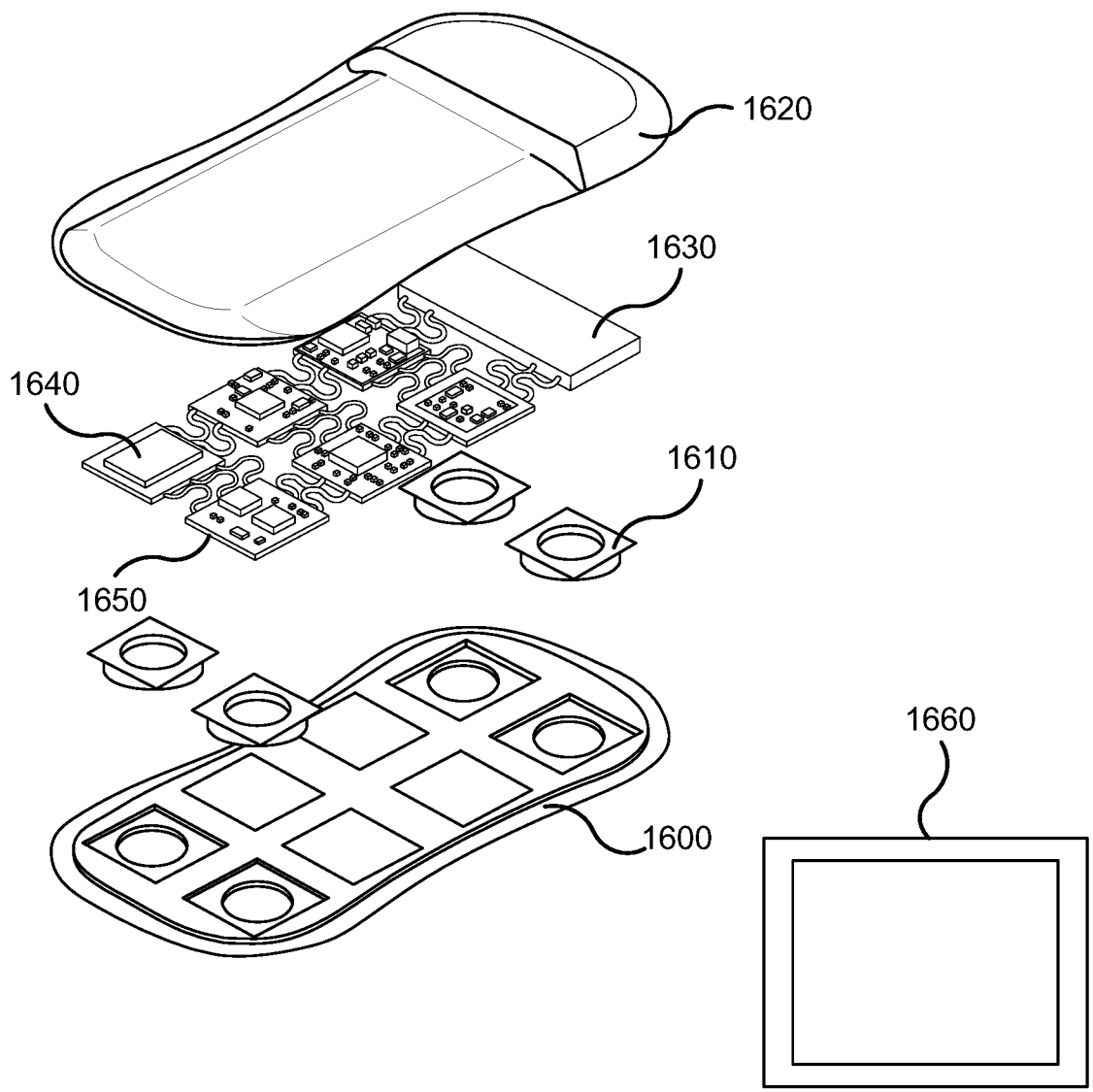
FIG. 16 provides a schematic of an example of the conformal device and optional monitor in wireless communication with the conformal device.
Figure 17:
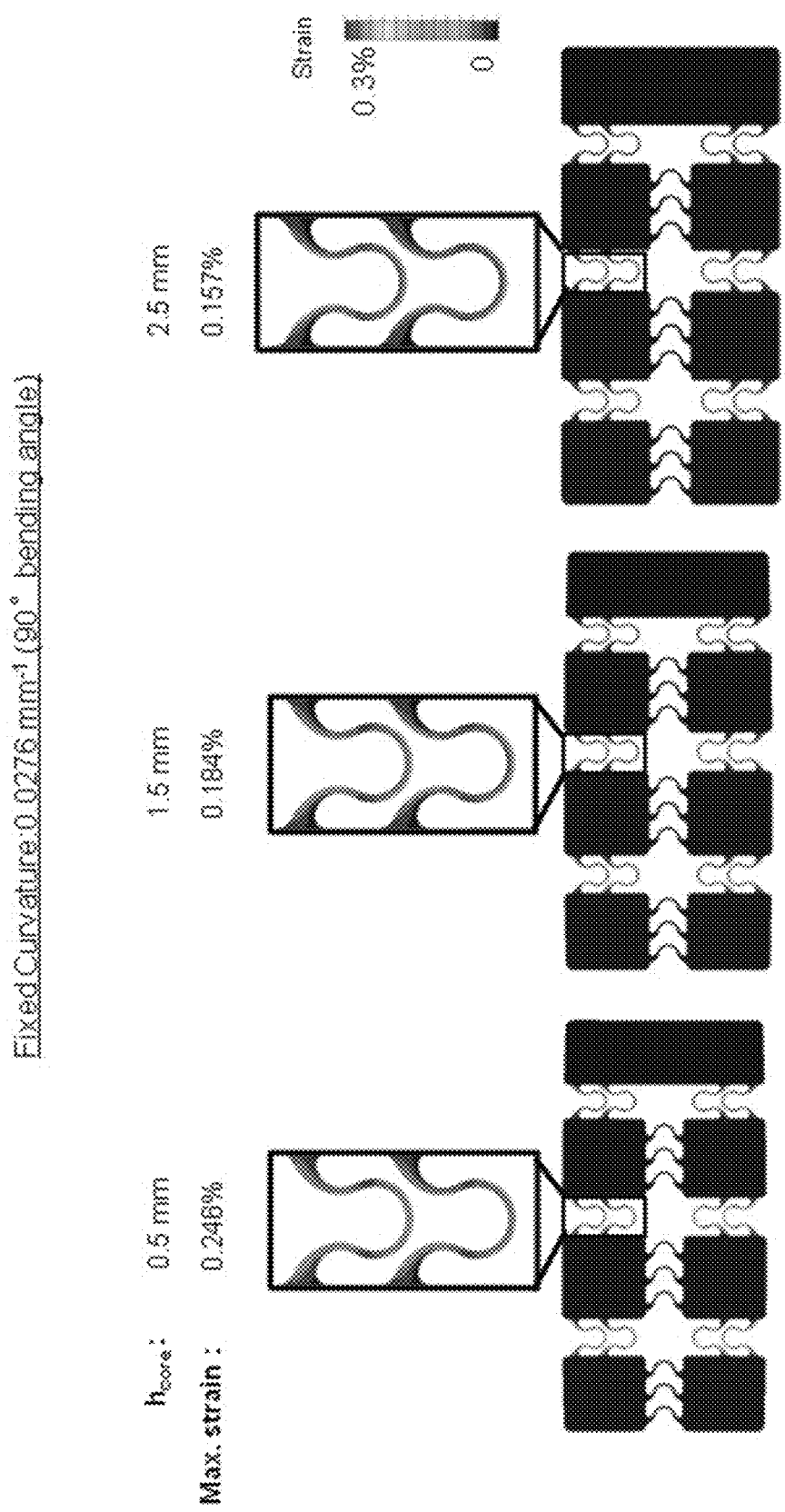
FIG. 17 provides spatial distribution of strain in the circuit elements in response to a fixed curvature and bending angle for different $h_{core}$ and the maximum strain that results.
Figures 18A, 18B, 18C:
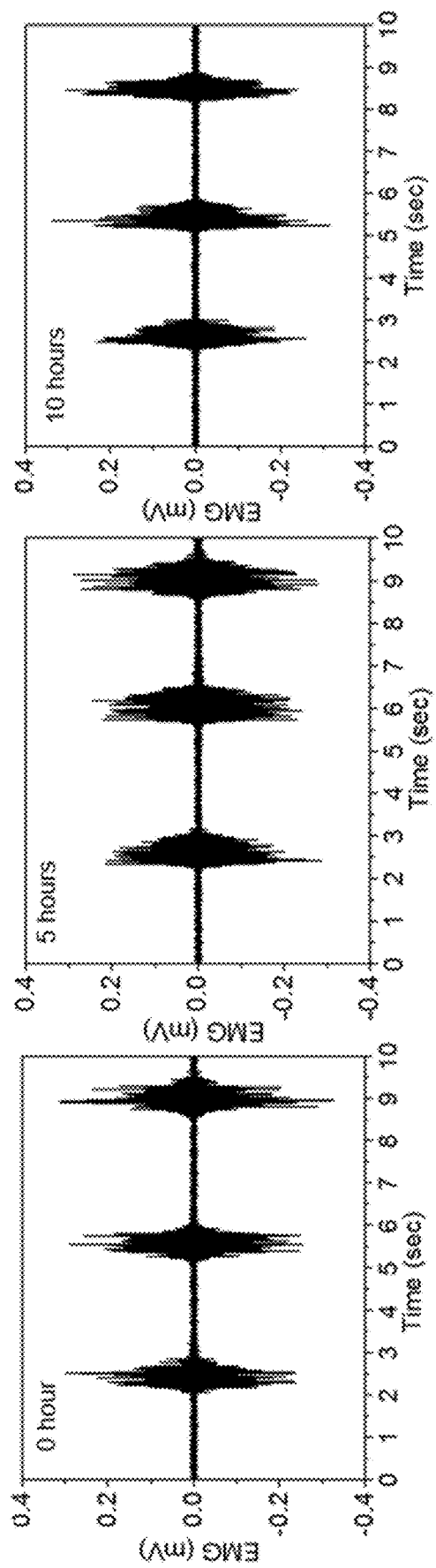
FIGS. 18A-18C illustrate recording stability of the conformable devices described herein. The clinical recording stability of the conformable device over the duration of a typical surgery is verified by EMG recordings during 10 hours of wearing. The signal amplitude and SNRs stimulated by maximum voluntary muscle contraction remains the same.

FIG. 16 provides a schematic of an example of the conformal device and optional monitor in wireless communication with the conformal device. The flexible substrate 1600 supports one or more sensors 1610 which are embedded in the flexible substrate, which is capable of establishing conformal contact with a tissue surface. A multilayer encapsulant 1620 forms the exterior of the device, away from the surface of conformal contact. The device may include an accelerometer and a gyroscope 1630, a battery 1640, and or an actuator 1650 to provide stimulation. Optionally, one or more of the conformal device is in wireless communication with a monitor 1660.

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

The following publications are specifically incorporated by reference for various methods of making, sensors, actuators, wireless power and control, and related components, configurations and mechanical characteristics associated with skin-mountable systems: Pub No. 2013/0041235A1, published Feb. 14, 2013, Application Ser. No. 13/492,636, filed Jun. 8, 2012; Pub No. WO 2017/004576, published Jan. 5, 2017; Appl No. PCT/US16/40814, filed Jul. 1, 2016; Pub No. WO 2016/025438, published Feb. 18, 2016, Appl No. PCT/US15/44588, filed Aug. 11, 2015; Pub No. WO 2016/025468, published Feb. 18, 2016; Appl No. PCT/US15/44638, filed Aug. 11, 2015; Pub No. WO 2016/196673, published Dec. 8, 2016; Appl No. PCT/US16/35331, filed Jun. 1, 2016; and Pub No. WO 2016/196675, published Dec. 8, 2016; Appl No. PCT/US16/35336, filed Jun. 1, 2016.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

As used herein and in the appended claims, the singular forms "a", "an", and "the" include plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure. For example, when a device is set forth disclosing a range of materials, device components, and/or device configurations, the description is intended to include specific reference of each combination and/or variation corresponding to the disclosed range.

Every formulation or combination of components described or exemplified herein can be used to practice the invention, unless otherwise stated.

Whenever a range is given in the specification, for example, a density range, a number range, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES

1. N. G. Simon, R. J. Spinner, D. G. Kline, M. Kliot, Advances in the neurological and neurosurgical management of peripheral nerve trauma. *Journal of Neurology, Neurosurgery & Psychiatry*, jnnp (2015).
2. P. J. Dyck, *Peripheral neuropathy*. (Elsevier Inc., 2005).
3. R. Kakazu, S. K. Dailey, A. J. Schroeder, J. D. Wyrick, M. T. Archdeacon, Iatrogenic Radial Nerve Palsy After Humeral Shaft Nonunion Repair: More Common Than You Think. *Journal of orthopaedic trauma* 30, 256 (2016).
4. G. Koch, A. Kling, N. Ramamurthy, F. Edalat, R. L. Cazzato, J.-L. Kahn, J. Garnon, P. Clavert, Anatomical risk evaluation of iatrogenic injury to the infrapatellar branch of the saphenous nerve during medial meniscus arthroscopic surgery. *Surgical and Radiologic Anatomy*, 1 (2016).
5. A. E. Weber, J. D. Harris, S. J. Nho, Complications in hip arthroscopy: a systematic review and strategies for prevention. *Sports medicine and arthroscopy review* 23, 187 (2015).
6. W. Kneist, D. Kauff, V. Juhre, K. Hoffmann, H. Lang, Is intraoperative neuromonitoring associated with better functional outcome in patients undergoing open TME?: Results of a case-control study. *European Journal of Surgical Oncology (EJSO)* 39, 994 (2013).
7. C. R. Falyar, K. M. Shaffer, R. A. Perera, Localization of the brachial plexus: sonography versus anatomic landmarks. *Journal of Clinical Ultrasound* 44, 411 (2016).
8. R. M. Ajiboye, A. D'oro, A. O. Ashana, R. A. Buerba, E. L. Lord, Z. Buser, J. C. Wang, S. Pourtaheri, Routine Use of Intraoperative Neuromonitoring During ACDFs for the Treatment of Spondylotic Myelopathy and Radiculopathy Is Questionable: A Review of 15,395 Cases. *Spine* 42, 14 (2017).
9. A. Mian, I. Chaudhry, R. Huang, E. Rizk, R. S. Tubbs, M. Loukas, Brachial plexus anesthesia: a review of the relevant anatomy, complications, and anatomical variations. *Clinical Anatomy* 27, 210 (2014).
10. V. Deletis, F. Sala, Intraoperative neurophysiological monitoring of the spinal cord during spinal cord and spine surgery: a review focus on the corticospinal tracts. *Clinical neurophysiology* 119, 248 (2008).
11. A. Koht, T. B. Sloan, J. R. Toleikis, *Monitoring the nervous system for anesthesiologists and other health care professionals*. (Springer, 2012).
12. A. R. Møller, *Intraoperative neurophysiological monitoring*. (Springer, 2006).
13. M. Hermann, C. Hellebart, M. Freissmuth, Neuromonitoring in thyroid surgery: prospective evaluation of intraoperative electrophysiological responses for the prediction of recurrent laryngeal nerve injury. *Annals of surgery* 240, 9 (2004).
14. D. Cypher, N. Chevrollier, N. Montavont, N. Golmie, Prevailing over wires in healthcare environments: benefits and challenges. *IEEE Communications Magazine* 44, 56 (2006).
15. A. Al-Shekhlee, B. E. Shapiro, D. C. Preston, Iatrogenic complications and risks of nerve conduction studies and needle electromyography. *Muscle & nerve* 27, 517 (2003).
16. S. L. Lynch, A. J. Boon, J. Smith, C. M. Harper, E. M. Tanaka, Complications of needle electromyography: hematoma risk and correlation with anticoagulation and antiplatelet therapy. *Muscle & nerve* 38, 1225 (2008).
17. Y. Liu, J. J. Norton, R. Qazi, Z. Zou, K. R. Ammann, H. Liu, L. Yan, P. L. Tran, K.-I. Jang, J. W. Lee, Epidermal mechano-acoustic sensing electronics for cardiovascular diagnostics and human-machine interfaces. *Science Advances* 2, e1601185 (2016).
18. S. Xu, Y. Zhang, L. Jia, K. E. Mathewson, K.-I. Jang, J. Kim, H. Fu, X. Huang, P. Chava, R. Wang, Soft microfluidic assemblies of sensors, circuits, and radios for the skin. *Science* 344, 70 (2014).
19. D.-H. Kim, N. Lu, R. Ma, Y.-S. Kim, R.-H. Kim, S. Wang, J. Wu, S. M. Won, H. Tao, A. Islam, Epidermal electronics. *Science* 333, 838 (2011).
20. C. H. Lee, Y. Ma, K. I. Jang, A. Banks, T. Pan, X. Feng, J. S. Kim, D. Kang, M. S. Raj, B. L. McGrane, Soft core/shell packages for stretchable electronics. *Advanced Functional Materials* 25, 3698 (2015).
21. A. Documentation, ABAQUS Analysis User's Manual. Materials. Other plasticity models. Concrete 113, (2010).
22. W. F. Riley, *Mechanics of Materials*. (John Wiley & Sons, Incorporated, 2006).
23. C. J. De Luca, A. Adam, R. Wotiz, L. D. Gilmore, S. H. Nawab, Decomposition of surface EMG signals. *Journal of neurophysiology* 96, 1646 (2006).
24. R. Merletti, M. Knaflitz, C. J. De Luca, Electrically evoked myoelectric signals. *Critical Reviews in Biomedical Engineering* 19, 293 (1992).
25. F. Rattay, *Electrical nerve stimulation*. (Springer, 1990).
26. P. H. Gorman, J. T. Mortimer, The effect of stimulus parameters on the recruitment characteristics of direct nerve stimulation. *IEEE Transactions on Biomedical Engineering*, 407 (1983).
27. C. Keyl, T. Held, G. Albiez, A. Schmack, C. Wiesenack, Increased electrical nerve stimulation threshold of the sciatic nerve in patients with diabetic foot gangrene: a prospective parallel cohort study. *European Journal of Anaesthesiology (EJA)* 30, 435 (2013).
28. K. P. Tschopp, C. Gottardo, Comparison of various methods of electromyographic monitoring of the recurrent laryngeal nerve in thyroid surgery. *Annals of Otology, Rhinology & Laryngology* 111, 811 (2002).
29. F. Radtke, M. Franck, J. Lendner, S. Kruger, K. Wernecke, C. Spies, Monitoring depth of anaesthesia in a randomized trial decreases the rate of postoperative delirium but not postoperative cognitive dysfunction. *British journal of anaesthesia* 110, i98 (2013).
30. M. Sutter, O. Hersche, M. Leunig, T. Guggi, J. Dvorak, A. Eggspuehler, Use of multimodal intra-operative monitoring in averting nerve injury during complex hip surgery. *The Journal of Bone and Joint Surgery—British Volume* 94, 179 (2012).
31. S. R. Thilen, S. M. Bhananker, Qualitative Neuromuscular Monitoring: How to Optimize the Use of a Peripheral Nerve Stimulator to Reduce the Risk of Residual Neuromuscular Blockade. *Current anesthesiology reports* 6, 164 (2016).
32. M. Kaltenbrunner, T. Sekitani, J. Reeder, T. Yokota, K. Kuribara, T. Tokuhara, M. Drack, R. Schwödiauer, I. Graz, S. Bauer-Gogonea, An ultra-lightweight design for imperceptible plastic electronics. *Nature* 499, 458 (2013).
33. R. C. Webb, Y. Ma, S. Krishnan, Y. Li, S. Yoon, X. Guo, X. Feng, Y. Shi, M. Seidel, N. H. Cho, Epidermal devices for noninvasive, precise, and continuous mapping of macrovascular and microvascular blood flow. *Science Advances* 1, e1500701 (2015).
34. C. Dagdeviren, Y. Su, P. Joe, R. Yona, Y. Liu, Y.-S. Kim, Y. Huang, A. R. Damadoran, J. Xia, L. W. Martin, Conformable amplified lead zirconate titanate sensors with enhanced piezoelectric response for cutaneous pressure monitoring. *Nature Communications* 5, (2014).
35. G. Schwartz, B. C.-K. Tee, J. Mei, A. L. Appleton, D. H. Kim, H. Wang, Z. Bao, Flexible polymer transistors with high pressure sensitivity for application in electronic skin and health monitoring. *Nature Communications* 4, 1859 (2013).
36. R. C. Webb, A. P. Bonifas, A. Behnaz, Y. Zhang, K. J. Yu, H. Cheng, M. Shi, Z. Bian, Z. Liu, Y.-S. Kim, Ultrathin conformal devices for precise and continuous thermal characterization of human skin. *Nature Materials* 12, 938 (2013).
37. X. Huang, Y. Liu, K. Chen, W. J. Shin, C. J. Lu, G. W. Kong, D. Patnaik, S. H. Lee, J. F. Cortes, J. A. Rogers, Stretchable, wireless sensors and functional substrates for epidermal characterization of sweat. *Small* 10, 3083 (2014).
38. S. Krishnan, Y. Shi, R. C. Webb, Y. Ma, P. Bastien, K. E. Crawford, A. Wang, X. Feng, M. Manco, J. Kurniawan, Multimodal epidermal devices for hydration monitoring. *Microsystems & Nanoengineering* 3, 17014 (2017).
39. C. Dagdeviren, Y. Shi, P. Joe, R. Ghaffari, G. Balooch, K. Usgaonkar, O. Gur, P. L. Tran, J. R. Crosby, M. Meyer, Conformal piezoelectric systems for clinical and experimental characterization of soft tissue biomechanics. *Nature Materials* 14, 728 (2015).
40. X. Huang, Y. Liu, H. Cheng, W. J. Shin, J. A. Fan, Z. Liu, C. J. Lu, G. W. Kong, K. Chen, D. Patnaik, Materials and designs for wireless epidermal sensors of hydration and strain. *Advanced Functional Materials* 24, 3846 (2014).
41. C. M. Boutry, A. Nguyen, Q. O. Lawal, A. Chortos, S. Rondeau-Gagne, Z. Bao, A sensitive and biodegradable pressure sensor array for cardiovascular monitoring. *Advanced Materials* 27, 6954 (2015).
42. M. Capogrosso, T. Milekovic, D. Borton, F. Wagner, E. M. Moraud, J.-B. Mignardot, N. Buse, J. Gandar, Q. Barraud, D. Xing, A brain-spine interface alleviating gait deficits after spinal cord injury in primates. *Nature* 539, 284 (2016).
43. W. Gao, S. Emaminejad, H. Y. Y. Nyein, S. Challa, K. Chen, A. Peck, H. M. Fahad, H. Ota, H. Shiraki, D. Kiriya, Fully integrated wearable sensor arrays for multiplexed in situ perspiration analysis. *Nature* 529, 509 (2016).
44. D. Khodagholy, J. N. Gelinas, T. Thesen, W. Doyle, O. Devinsky, G. G. Malliaras, G. Buzsáki, NeuroGrid: recording action potentials from the surface of the brain. *Nature neuroscience* 18, 310 (2015).
45. C. M. Lochner, Y. Khan, A. Pierre, A. C. Arias, All-organic optoelectronic sensor for pulse oximetry. *Nature Communications* 5, (2014).
46. T. Yokota, P. Zalar, M. Kaltenbrunner, H. Jinno, N. Matsuhisa, H. Kitanosako, Y. Tachibana, W. Yukita, M. Koizumi, T. Someya, Ultraflexible organic photonic skin. *Science Advances* 2, el 501856 (2016).
47. Gamble P, Stephen M, Mac Ewan M, Ray WZ Serial assessment of functional recovery following nerve injury using implantable thin-film wireless nerve stimulators. *Muscle Nerve* 54, 11141119 (2016).
48. MacEwan M, Gamble P, Stephen M, Ray WZ Therapeutic electrical stimulation of injured peripheral nerve tissue utilizing implantable thin-film wireless nerve stimulators. *Journal of Neurosurgery* 84, (2017)

We claim:

1. A method of characterizing a neuromuscular property of a subject comprising:
   providing a conformable device comprising:
      a flexible or stretchable substrate; and
      a sensor supported by said flexible or stretchable substrate; said sensor comprising a plurality of electrodes for measuring electric potentials of a tissue of said subject;
      wherein said flexible or stretchable substrate and said sensor provide a net bending stiffness such that the device is capable of establishing conformal contact with a receiving surface of the tissue;
   contacting said device with said receiving surface of the tissue, wherein said contacting results in said conformal contact of at least a portion of said device with said surface of the tissue; and
   measuring a temporal profile of said electric potentials of the tissue with said plurality of electrodes; thereby characterizing said neuromuscular property, wherein said characterization of said neuromuscular property provides a real-time clinical metric.

2. The method of claim 1 providing a method for sensing an electromyography signal of said subject.

3. The method of claim 1, wherein said neuromuscular property is one or more of threshold current of electrical nerve stimulation, response to direct electrical stimulation of said tissue, spontaneous muscle activity corresponding to a level of anesthesia of said subject, and depth of paralysis.

4. The method of claim 1, wherein said conformable device is capable of stretching, twisting, or bending without altering functional operation and signal fidelity.

5. The method of claim 1, wherein said temporal profile of said electric potentials provide measurement of an electromyography (EMG) waveform.

6. The method of claim 5, further comprising analyzing the EMG waveforms.

7. The method of claim 6, wherein said temporal profile of said electric potentials provide a surface electromyography (s-EMG) measurement.

8. The method of claim 1, wherein said electrodes comprise at least a pair of Ag/AgCl electrodes or ENIG/AU electrodes.

9. The method of claim 1, wherein said sensor of said conformal device is a multimodal sensor; said method further comprising sensing of a plurality of tissue properties or conditions.

10. The method of claim 1, further comprises measuring one or more properties selected from the group consisting of tissue position, tissue movement, blood flow, blood pressure, a temperature, hydration state, tissue stiffness, mechano-acoustic signatures, and swelling.

11. The method of claim 1, wherein said sensor of said conformal device further comprises a motion detector supported by said substrate; said method further comprising the step of measuring a temporal profile of the position, movement or both of said tissue.

12. The method of claim 11, wherein said motion detector comprises an accelerometer, a gyroscope or both.

13. The method of claim 1, wherein said characterization of said neuromuscular property triggers a downstream clinical response.

14. The method of claim 1, further comprising:
providing a stimulating conformable device comprising:
a second flexible or stretchable substrate;
an actuator for electrically stimulating said tissue of said subject, supported by said second flexible or stretchable substrate; and
wherein said second flexible or stretchable substrate and said actuator provide a net bending stiffness such that the device is capable of establishing conformal contact with said receiving surface of the tissue;
contacting said stimulating conformal device with said receiving surface of the tissue, wherein contact results in said conformal contact of at least a portion of said stimulating conformal device with said surface of the tissue; and
stimulating said tissue using said actuator and simultaneously measuring a temporal profile of electric potentials of said tissue with said plurality of electrodes in response to said stimulation.

15. The method of claim 1, wherein said conformal device further comprises an actuator, and said method further comprises:
electrically stimulating said tissue using said actuator and simultaneously measuring a temporal profile of electric potentials of said subject with said plurality of electrodes in response to said electrical stimulation.

16. The method of claim 15, wherein said characterization of said neuromuscular property is time-synced to said stimulation.

17. The method of claim 15, wherein said stimulation further comprises thermal stimulation, acoustic stimulation or any combination of these.

18. The method of claim 15, wherein said characterization triggers a downstream clinical response.

19. The method of claim 1, wherein said conformal device further comprises a thermal actuator, said method further comprises providing a thermal stimulation of the tissue of said subject.

20. The method of claim 1, wherein said sensor of said conformable device has a stretchable or flexible island interconnect geometry.

21. The method of claim 20, wherein said stretchable or flexible island interconnect geometry is characterized by a plurality of functional device components electrically interconnected via filamentary serpentine traces.

22. The method of claim 1, wherein said device further comprises a one-way or two-way wireless component supported by said substrate and operationally connected to said sensor.

23. The method of claim 22, wherein said wireless component is a wireless transmitter supported by said substrate; said method further comprising outputting signals corresponding to said temporal profile of electric potentials.

24. The method of claim 22, wherein said wireless component is a wireless receiver supported by said substrate; said method further comprising for receiving a signal from a user, a monitor or a device.

25. The method of claim 24, wherein said wireless receiver is operably connected to an external device for providing closed loop feedback control of said conformal device.

26. The method of claim 24, wherein said wireless receiver is operably connected to an external device for providing audio/visual feedback to the operator on the status of nerves or muscle contraction.

27. The method of claim 26, wherein said external device is a smartphone, a laptop computer, a desktop computer, a tablet, a speaker, a wearable electronic or a console.

28. The method of claim 1, wherein said device further comprises a rechargeable battery providing power to said conformable device.

29. The method of claim 1, further comprising providing one or more hydrogel layers or conductive gel layers between the tissue and said conformal device.

30. The method of claim 1, wherein said tissue is external tissue, or internal tissue.

31. The method of claim 30, wherein said tissue is skin, nervous system tissue, peripheral nerves, muscle, or spinal cord.

32. The method of claim 1, wherein a plurality of said conformal devices are provided to a variety of receiving surface corresponding to tissues of said subject; said method further comprising measuring a plurality of temporal profiles of electric potentials of said tissues; thereby characterizing said neuromuscular property.

33. The method of claim 1, further comprising a plurality of conformable devices, wherein the step contacting independently contacts each of the devices with one or more receiving surfaces of one or more tissues.

34. The method of claim 33, wherein the plurality of conformable devices comprise:
a conformable device capable of measuring an electrocardiogram;
a conformable device capable of measuring an electrooculogram; and
a conformable device capable of measuring an electromyogram.

35. The method of claim 33, wherein the plurality of conformable devices are time-synched.

36. The method of claim 33, wherein the plurality of conformable devices form a closed-loop system.

37. A conformable device comprising:
a flexible or stretchable substrate;
a sensor supported by said flexible or stretchable substrate; said sensor comprising plurality of electrodes for measuring electric potentials of a tissue of said subject; and
a multilayer encapsulant at least partially encapsulating said sensor; said multilayer encapsulant comprising a lower modulus core layer at least partially embedding said sensor and a higher modulus shell at least partially surrounding said a first lower modulus core layer and sensor; wherein said lower modulus core layer has a Young's modulus at least 10 times lower than that of said higher modulus shell;
wherein said flexible or stretchable substrate, sensor and multilayer encapsulant provide a net bending stiffness such that the device is capable of establishing conformal contact with a receiving surface of a tissue of a subject; and
wherein said lower modulus core layer is characterized by an average Young's modulus selected over the range of 1 kPa-100 kPa.

38. The device of claim 37, wherein said lower modulus core layer has an average thickness selected over the range of 2 microns to 2 millimeters.

39. The device of claim 37, wherein said higher modulus shell is characterized by an average Young's modulus equal to or less than 2 MPa.

40. The device of claim 37, wherein said higher modulus shell is characterized by an average Young's modulus selected over the range of 50 kPa-2 MPa.

41. The device of claim 37, wherein said higher modulus core layer has an average thickness selected over the range of 10 microns to 2 millimeters.

42. The device of claim 37, wherein said lower modulus core layer and said higher modulus shell each independently comprise a silicone composition.

43. The device of claim 37, wherein said lower modulus core layer and said higher modulus shell combine to provide an effective modulus of said conformal device of less than or equal to 2 MPa.

44. The device of claim 37, wherein said sensor is a multimodal sensor.

45. The device of claim 37, wherein said sensor further comprises one or more additional components for measuring one or more properties selected from the group consisting of tissue position, tissue movement, blood flow, blood pressure, a temperature, hydration state, tissue stiffness, mechano-acoustic signatures, and swelling.

46. The device of claim 37, wherein said sensor further comprises a motion detector for measuring a temporal profile of the position, movement or both of said tissue.

47. The device of claim 46, wherein said motion detector comprises an accelerometer, a gyroscope or both.

48. The device of claim 37, wherein said electrodes comprise at least a pair of Ag/AgCl electrodes or ENIG/AU electrodes.

49. The device of claim 37, wherein said conformal device further comprises an actuator for providing a stimulation of the tissue of said subject.

50. The device of claim 37, wherein said stimulation is electrical actuation, thermal actuation, acoustic actuation or any combination of these.

51. The device of claim 37, wherein said sensor of said conformable device has a stretchable or flexible island interconnect geometry.

52. The device of claim 37, wherein said stretchable or flexible island interconnect geometry is characterized by a plurality of functional device components electrically interconnected via filamentary serpentine traces.

53. The device of claim 37, wherein said device further comprises a one-way or two-way wireless component supported by said substrate and operationally connected to said sensor.

54. The device of claim 37, wherein said wireless component is a wireless transmitter supported by said substrate for outputting signals corresponding to said temporal profile of electric potentials.

55. The device of claim 37, wherein said wireless component is a wireless receiver supported by said substrate for receiving a signal from a user.

56. The device of claim 37, further comprising one or more hydrogel layers.

57. The device of claim 56, wherein said one or more hydrogel layers is characterized by an average thickness selected from the range of 0.1 millimeters to 2 millimeters.

58. The device of claim 56, wherein said one or more hydrogel layers is characterized by an average Young's modulus selected from the range of 1 kPa to 100 kPa.

59. The device of claim 56, wherein said one or more hydrogel layers is characterized by an electrical conductivity selected from the range of 0.1 S/m to 0.8 S/m.

60. A method of monitoring a level of anesthesia of a subject comprising:
providing a conformable device comprising:
a flexible or stretchable substrate; and
a sensor supported by said flexible or stretchable substrate; said sensor comprising plurality of electrodes for measuring electric potentials of a tissue of said subject;
wherein said flexible or stretchable substrate and sensor provide a net bending stiffness such that the device is capable of establishing conformal contact with a receiving surface of the tissue;
contacting the device with said receiving surface of the tissue, wherein contact results in said conformal contact of at least a portion of said device with said surface of the tissue;
measuring a temporal profile of electric potentials of said tissue with said plurality of electrodes corresponding to spontaneous muscle activity; and
monitoring said spontaneous muscle activity in real time during an operation, wherein said spontaneous muscle activity corresponds to said level of anesthesia of said subject,
wherein said monitoring said spontaneous muscle activity provides a real-time clinical metric.

61. The method of claim 60 further comprising:
treating said subject with a paralytic agent to prevent spontaneous movement of said tissue;
wherein said step of monitoring spontaneous muscle activity further comprises monitoring a depth of a paralysis of said tissue.

62. The method of claim 60, wherein said real-time clinical metric triggers a downstream clinical response.

63. A method of promoting nerve recovery of a subject comprising:
providing a sensing conformable device comprising:
a flexible or stretchable substrate;
a sensor supported by said flexible or stretchable substrate; said sensor comprising plurality of electrodes for measuring electric potentials of a tissue of said subject; and
wherein said flexible or stretchable substrate and sensor provide a net bending stiffness such that the device is capable of establishing conformal contact with a receiving surface of the tissue;
providing a stimulating conformable device comprising:
a second flexible or stretchable substrate;
an actuator for stimulating said tissue of said subject, supported by said second flexible or stretchable substrate; and
wherein said second flexible or stretchable substrate and said actuator provide a net bending stiffness such that the device is capable of establishing conformal contact with said receiving surface of the tissue;
contacting said flexible device and said stimulating conformal device with said receiving surface of the tissue, wherein contact results in said conformal contact of at least a portion of said flexible device and said stimulating conformal device with said receiving surface of the tissue; and
stimulating said tissue using said actuator and simultaneously measuring a neuromuscular property in response to said stimulation, wherein stimulation of said tissue promotes nerve recovery in said tissue,
wherein said actuation is electrical actuation, thermal actuation, acoustic actuation or any combination of these.

64. The method of claim 63, wherein said nerve recovery in said tissue is axonal regeneration, inhibition of demyelination, promotion of remyelination, secretion of a trophic factor or a combination thereof.

65. The method of claim 63, wherein said sensor and said actuator are supported by the same substrate and a single conformable device senses and stimulates.

66. A method of characterizing a neuromuscular property of a subject comprising:
   providing a conformable device comprising:
      a flexible or stretchable substrate;
      at least one actuator for providing electrical stimulation; and
      a sensor supported by said flexible or stretchable substrate; said sensor comprising plurality of electrodes;
      wherein said flexible or stretchable substrate and sensor provide a net bending stiffness such that the device is capable of establishing conformal contact with a receiving surface of a tissue of the subject;
   contacting the device with said receiving surface of the tissue, wherein contact results in said conformal contact of at least a portion of said device with said surface of the tissue;
   establishing electrical communication between said actuator and a nerve of the subject, wherein said contact is established by internal contact of said actuator with said nerve of said subject, by external contact of said actuator with said tissue of the subject or a combination thereof;
   stimulating said nerve via said actuator and measuring a temporal profile of electric potentials of said tissue or said nerve with said plurality of electrodes; thereby characterizing said neuromuscular property; and
   monitoring and confirming effective electrical stimulation of said tissue or said nerve.

67. A method of detecting muscle reinnervation of a subject comprising:
   providing a conformable device comprising:
      a flexible or stretchable substrate; and
      a sensor supported by said flexible or stretchable substrate; said sensor comprising plurality of electrodes for measuring electric potentials of a tissue of said subject;
      wherein said flexible or stretchable substrate and sensor provide a net bending stiffness such that the device is capable of establishing conformal contact with a receiving surface of the tissue;
   contacting the device with said receiving surface of the tissue, wherein contact results in said conformal contact of at least a portion of the device with said receiving surface of the tissue; and
   measuring a temporal profile of electric potentials of said tissue with said plurality of electrodes; thereby characterizing said muscle reinnervation,
   wherein said method is post-operative.

68. The method of claim 67, wherein said conformal contact involves direct physical contact between one or more contact surfaces of the device and said receiving surface of the tissue.

69. The method of claim 67, wherein said conformal contact involves indirect contact between one or more contact surfaces of the device and said receiving surface of the tissue.

70. The method of claim 67, wherein said conformal contact involves direct physical contact or indirect contact between one or more contact surfaces of the device and said receiving surface of a surface of a skin of a subject.

71. The method of claim 67, wherein said conformal contact involves direct physical contact or indirect contact between one or more contact surfaces of the device and said receiving surface of an internal tissue of a subject.

72. The method of claim 71, wherein said internal tissue is peripheral nerves, muscle, or spinal cord tissue.

* * * * *